(12) United States Patent
Yu et al.

(10) Patent No.: US 11,299,744 B2
(45) Date of Patent: Apr. 12, 2022

(54) TRANSGENIC PLANTS EXPRESSING TYPE 2C PROTEIN PHOSPHATASE ABSCISIC ACID (PP2CABA) PROTEINS AND USES THEREOF

(71) Applicant: Academia Sinica, Taipei (TW)

(72) Inventors: Su-May Yu, Taipei (TW); Chun-Hsien Lu, Taipei (TW); Tuan-Hua David Ho, Taipei (TW); Shuen-Fang Lo, Taichung County (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 15/838,702

(22) Filed: Dec. 12, 2017

(65) Prior Publication Data

US 2018/0163221 A1 Jun. 14, 2018

Related U.S. Application Data

(60) Provisional application No. 62/433,212, filed on Dec. 12, 2016.

(51) Int. Cl.
*C12N 15/82* (2006.01)
*C12N 9/16* (2006.01)

(52) U.S. Cl.
CPC .......... *C12N 15/8273* (2013.01); *C12N 9/16* (2013.01); *C12N 15/82* (2013.01); *C12N 15/8255* (2013.01); *C12N 15/8261* (2013.01); *C12N 15/8271* (2013.01); *Y02A 40/146* (2018.01)

(58) Field of Classification Search
None
See application file for complete search history.

(56) References Cited

U.S. PATENT DOCUMENTS

| | | |
|---|---|---|
| 7,569,389 B2 | 8/2009 | Feldmann et al. |
| 8,759,614 B2 | 6/2014 | Yu et al. |
| 2004/0031072 A1 | 2/2004 | La Rosa et al. |
| 2006/0123505 A1* | 6/2006 | Kikuchi ............... C07K 14/415 800/278 |
| 2007/0039067 A1 | 2/2007 | Feldmann et al. |
| 2010/0017919 A1 | 1/2010 | Zhang et al. |
| 2016/0016023 A1 | 6/2016 | Yu et al. |

FOREIGN PATENT DOCUMENTS

| | | |
|---|---|---|
| CN | 102465130 A | 5/2012 |
| CN | 103408648 A | 11/2013 |
| CN | 103421815 A | 12/2013 |
| CN | 103451228 A | 12/2013 |
| JP | 2005-185101 A | 7/2005 |
| WO | WO-2014113605 A1 * | 7/2014 ........... C07K 14/415 |
| WO | WO 2015/181823 A1 | 12/2015 |

OTHER PUBLICATIONS

UniProtKB-Q5Z6F5, OsPP2C59, Protein phosphatase 2C 59, Feb. 10, 2009 (Year: 2009).*
Kasuga et al. (Nature Biotechnology, vol. 17, pp. 287-291, Mar. 1999).*
Tanaka et al. (NCBI, GenBank Sequence Accession No. Q5Z6F5; Published Mar. 2, 2010).*
Kyoko et al. (FEBS Letters, 428:275-280, 1998).*
Genbank Accession No. ACX24980, version ACX24980.1; Sequence 56491 from U.S. Pat. No. 7,569,389. Feldmann et al.; Sep. 28, 2009. 1 page.
Genbank Accession No. HV077276, version HV077276.1; JP2005185101-A/12154: Full length cDNA of plant and the use thereof. Ishikawa et al.; Jul. 15, 2011. 1 page.
Genbank Accession No. BAF20378, version BAF20378.1; Os06g0698300 [*Oryza sativa* Japonica Group]. Matsumoto et al.; Aug. 11, 2012. 3 pages.
Genbank Accession No. XP_021304510, version XP_021304510.1. Probable protein phosphatase 2C 59 isoform X2 [Sorghum bicolor]. Jun. 13, 2017. 2 pages.
Genbank Accession No. XP_004966135, version XP_004966135.1. Probable protein phosphatase 2C 59 [Setaria italica]. Oct. 13, 2017. 2 pages.
Genbank Accession No. EMS67352, version EMS67352.1. Putative protein phosphatase 2C 59 [Triticum urartu]. Mar. 20, 2015. 2 pages.
Genbank Accession No. XP_015626502, version XP_015626502.1. Probable protein phosphatase 2C 10 isoform X2 [*Oryza sativa* Japonica Group], Mar. 1, 2016. 2 pages.
Genbank Accession No. XP_015626501, version XP_015626501.1. Probable protein phosphatase 2C 10 isoform X2 [*Oryza sativa* Japonica Group], Aug. 7, 2018. 2 pages.
[No Author Listed] LOC_Os06g48300. Rice Genome Annotation Project. http://rice.plantbiology.msu.edu/cgi-bin/ORF_infopage.cgi?orf=LOC_Os06g48300.1. [Last accessed Nov. 17, 2020]. 4 pages.
Chen et al., A late embryogenesis abundant protein HVA1 regulated by an inducible promoter enhances root growth and abiotic stress tolerance in rice without yield penalty. Plant Biotechnol J. Jan. 2015;13(1):105-16. doi: 10.1111/pbi.12241. Epub Sep. 9, 2014.
Cutler et al., Abscisic acid: emergence of a core signaling network. Annu Rev Plant Biol. 2010;61:651-79. doi: 10.1146/annurev-arplant-042809-112122.
De Smet et al., Auxin-dependent regulation of lateral root positioning in the basal meristem of *Arabidopsis*. Development. Feb. 2007;134(4):681-90. doi: 10.1242/dev.02753. Epub Jan. 10, 2007.
Dubrovsky et al., Auxin acts as a local morphogenetic trigger to specify lateral root founder cells. Proc Natl Acad Sci U S A. Jun. 24, 2008;105(25):8790-4. doi: 10.1073/pnas.0712307105. Epub Jun. 16, 2008.
Enstone et al., Root Endodermis and Exodermis: Structure, Function, and Responses to the Environment. J Plant Growth Regul. 2003;21:335-351. DOI: 10.1007/s00344-003-0002-2.

(Continued)

*Primary Examiner* — Vinod Kumar
(74) *Attorney, Agent, or Firm* — Wolf, Greenfield & Sacks, P.C.

(57) ABSTRACT

The present disclosure relates to transgenic plants that over-express PP2CABA and methods of using such for enhancing osmotic stress tolerance.

7 Claims, 19 Drawing Sheets

Specification includes a Sequence Listing.

(56) References Cited

OTHER PUBLICATIONS

Fuchs et al., Type 2C protein phosphatases in plants. FEBS J. Jan. 2013;280(2):681-93. doi: 10.1111/j.1742-4658.2012.08670.X. Epub Jul. 17, 2012.

Himmelbach et al., Homeodomain protein ATHB6 is a target of the protein phosphatase ABI1 and regulates hormone responses in *Arabidopsis*. EMBO J. Jun. 17, 2002;21(12):3029-38. doi: 10.1093/emboj/cdf316.

Liu et al., Activation of Big Grain1 significantly improves grain size by regulating auxin transport in rice. Proc Natl Acad Sci U S A. Sep. 1, 2015;112(35):11102-7. doi:10.1073/pnas.1512748112. Erratum in: Proc Natl Acad Sci U S A. Sep. 29, 2015;112(39):E5446. Supporting Information.

López-Bucio et al., The role of nutrient availability in regulating root architecture. Curr Opin Plant Biol. Jun. 2003;6(3):280-7. doi: 10.1016/s1369-5266(03)00035-9.

Malamy, Intrinsic and environmental response pathways that regulate root system architecture. Plant Cell Environ. Jan. 2005;28(1):67-77. doi: 10.1111/j.1365-3040.2005.01306.x.

Moura et al., Abiotic and biotic stresses and changes in the lignin content and composition in plants. J Integr Plant Biol. Apr. 2010;52(4):360-76. doi: 10.1111/j.1744-7909.2010.00892.x.

Ouyang et al., The TIGR Rice Genome Annotation Resource: improvements and new features. Nucleic Acids Res. Jan. 2007;35(Database issue):D883-7. doi: 10.1093/nar/gkl976. Epub Dec. 1, 2006.

Peret et al., Lateral root emergence: a difficult birth. J Exp Bot. 2009;60(13):3637-43. doi: 10.1093/jxb/erp232. Epub Jul. 27, 2009.

Potters et al., Stress-induced morphogenic responses: growing out of trouble? Trends Plant Sci. Mar. 2007;12(3):98-105. doi: 10.1016/j.tplants.2007.01.004. Epub Feb. 6, 2007.

Price et al., Genetic dissection of root growth in rice (*Oryza sativa* L.). II: mapping quantitative trait loci using molecular markers. Theor Appl Genet. 1997;95:143-152.

Ranathunge et al., Stagnant deoxygenated growth enhances root suberization and lignifications, but differentially affects water and NaCl permeabilities in rice (*Oryza sativa* L.) roots. Plant Cell Environ. Aug. 2011;34(8):1223-40. doi: 10.1111/j.1365-3040.2011.02318.x. Epub Apr. 21, 2011.

Robbins et al., The divining root: moisture-driven responses of roots at the micro- and macro-scale. J Exp Bot. Apr. 2015;66(8):2145-54. doi: 10.1093/jxb/eru496. Epub Jan. 22, 2015.

Rogers et al., The genetic control of lignin deposition during plant growth and development. New Phytologist. 2004;164: 17-30.

Singh et al., Protein phosphatase complement in rice: genome-wide identification and transcriptional analysis under abiotic stress conditions and reproductive development. BMC Genomics. Jul. 16, 2010;11:435. doi: 10.1186/1471-2164-11-435.

Tiedemann et al., Dissection of a complex seed phenotype: novel insights of FUSCA3 regulated developmental processes. Dev. Biol. May 1, 2008;317(1):1-12. Epub Feb. 13, 2008.

Uga et al., Control of root system architecture by Deeper Rooting 1 increases rice yield under drought conditions. Nat Genet. Sep. 2013;45(9):1097-102. doi: 10.1038/ng.2725. Epub Aug. 4, 2013.

Xue et al., Genome-wide and expression analysis of protein phosphatase 2C in rice and *Arabidopsis*. BMC Genomics. Nov. 20, 2008;9:550. doi: 10.1186/1471-2164-9-550.

Yoshida et al., Omics Approaches Toward Defining the Comprehensive Abscisic Acid Signaling Network in Plants. Plant Cell Physiol. Jun. 2015;56(6):1043-52. doi: 10.1093/pcp/pcv060. Epub Apr. 26, 2015.

No Author Listed, Genbank Submission; NCBI, Accession No. XP_025881975, Version XP_025881975.1; probable protein phosphatase 2C 59 isoform X2 [*Oryza sativa* Japonica Group]. Aug. 7, 2018. 2 pages.

No Author Listed, Genbank Submission; NCBI, Accession No. XP_015643686, Version XP_015643686.1; probable protein phosphatase 2C 59 isoform X1 [*Oryza sativa* Japonica Group]. Aug. 7, 2018. 2 pages.

No Author Listed, Genbank Submission; NCBI, Accession No. XM_015788200, Version XM_015788200.2; Predicted: *Oryza sativa* Japonica Group probable protein phosphatase 2C 59(LOC4341949), transcript variant X1, mRNA. Aug. 7, 2018. 2 pages.

No Author Listed, Genbank Submission; NCBI, Accession No. XM_026026191, Version XM_026026191.1; Predicted: *Oryza sativa* Japonica Group probable protein phosphatase 2C 59(LOC4341949), transcript variant X3, mRNA. Aug. 7, 2018. 2 pages.

* cited by examiner

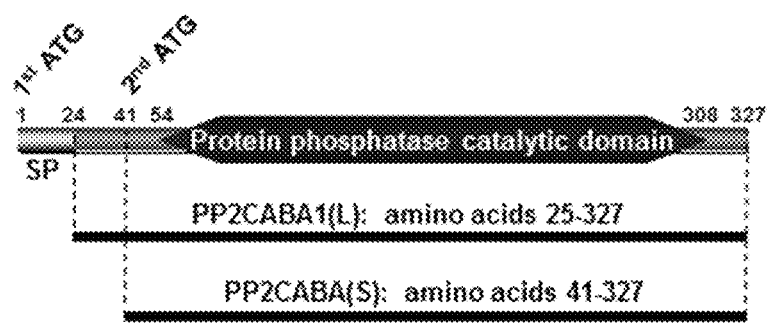
FIG. 6A
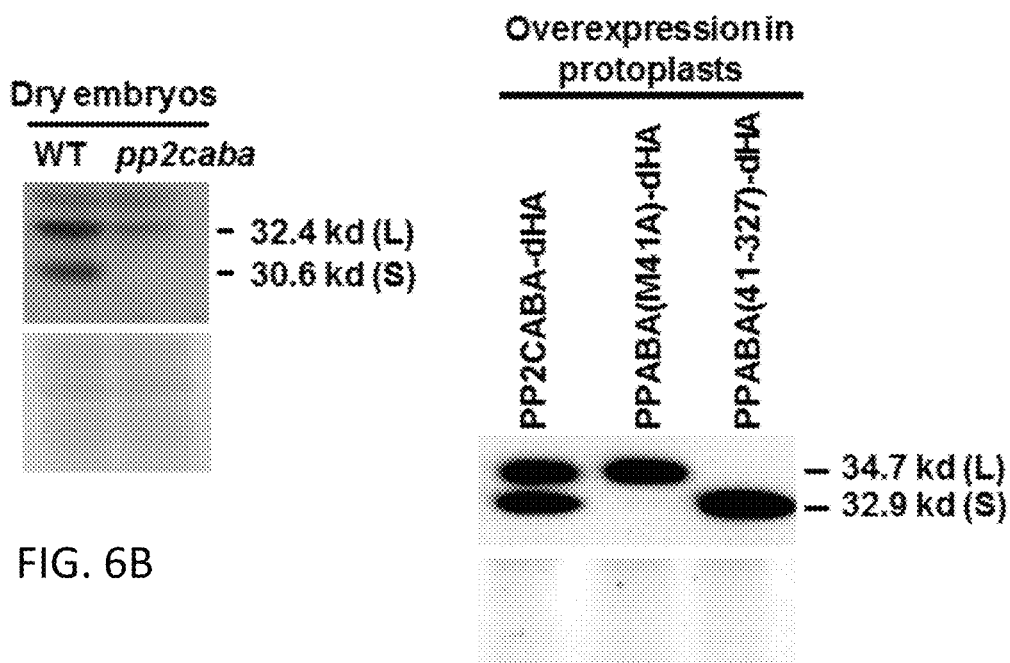
FIG. 6B
FIG. 6C

SEQUENCE LISTING

```
<160> NUMBER OF SEQ ID NOS: 52

<210> SEQ ID NO 1
<211> LENGTH: 984
<212> TYPE: DNA
<213> ORGANISM: Oryza sativa

<400> SEQUENCE: 1
atgcgtgagg tgctcctcct cggctcgttg gtggttctcg ccttgttgtc gctgttcccg     60
tgctgctcct gtctctcgca gggagcggag gaggaggagg acgacggcga ggtgcgcttg    120
atggggctcg ccggagaggc cgctggctcg cctggcagtg gcggcgggtt cagtgcaaat    180
ggtaaattta gctatggtta tgcgagctct cctggaaaaa gatcctccat ggaggacttc    240
tatgacacca gaattgatgg tgtcgatgga gagaccgttg gactgtttgg tgtctttgat    300
ggtcatggtg gagctcgagc agcagaattc gtcaagcaga acctcttcac caatttaatc    360
aagcacccaa agttattcag tgataccaag tctgcaattg ctgaaactta cactagcacg    420
gactctgaac ttctgaaagc tgaaaccagc cacaatcgag atgcagggtc gactgcctcc    480
actgcaattc tcgtaggcga ccgtctgctc gttgcaaatg ttggagattc tagggctgtc    540
atttgtagag gaggagatgc tatagctgtg tcaagagacc acaagcctga tcagtcagac    600
gagaggcaga ggatagagga tgctggtggt tttgtgatgt gggctggaac atggcgcgtg    660
ggtggtgttc ttgctgtctc tcgagcattt ggtgacaaac tcctgaagca atatgtggtt    720
gctgatccag agatcaagga ggaggtggtc gacagctctc tcgagttcct catccttgct    780
agtgatggcc tctgggacgt ggtgaccaac gaggaagctg tggccatggt gaagccaatt    840
ctggattcag agcaggctgc aaagaagctc ctccaggagg cctcacagag gggaagcgca    900
gacaacatca cctgcctcgt cgtccgtttc ttggagcagg agaatcacct gccagagaga    960
ccgacgaatg atcaagcctc ctaa                                          984

<210> SEQ ID NO 2
<211> LENGTH: 327
<212> TYPE: PRT
<213> ORGANISM: Oryza sativa

<400> SEQUENCE: 2

Met Arg Glu Val Leu Leu Leu Gly Ser Leu Val Val Leu Ala Leu Leu
 1               5                  10                  15

Ser Leu Phe Pro Cys Cys Ser Cys Leu Ser Gln Gly Ala Glu Glu Glu
            20                  25                  30

Glu Asp Asp Gly Glu Val Arg Leu Met Gly Leu Ala Gly Glu Ala Ala
        35                  40                  45

Gly Ser Pro Gly Ser Gly Gly Phe Ser Ala Asn Gly Lys Phe Ser
    50                  55                  60

Tyr Gly Tyr Ala Ser Ser Pro Gly Lys Arg Ser Ser Met Glu Asp Phe
65                  70                  75                  80
```

```
Tyr Asp Thr Arg Ile Asp Gly Val Asp Gly Glu Thr Val Gly Leu Phe
                 85                  90                  95

Gly Val Phe Asp Gly His Gly Gly Ala Arg Ala Ala Glu Phe Val Lys
            100                 105                 110

Gln Asn Leu Phe Thr Asn Leu Ile Lys His Pro Lys Leu Phe Ser Asp
        115                 120                 125

Thr Lys Ser Ala Ile Ala Glu Thr Tyr Thr Ser Thr Asp Ser Glu Leu
    130                 135                 140

Leu Lys Ala Glu Thr Ser His Asn Arg Asp Ala Gly Ser Thr Ala Ser
145                 150                 155                 160

Thr Ala Ile Leu Val Gly Asp Arg Leu Leu Val Ala Asn Val Gly Asp
                165                 170                 175

Ser Arg Ala Val Ile Cys Arg Gly Gly Asp Ala Ile Ala Val Ser Arg
            180                 185                 190

Asp His Lys Pro Asp Gln Ser Asp Glu Arg Gln Arg Ile Glu Asp Ala
        195                 200                 205

Gly Gly Phe Val Met Trp Ala Gly Thr Trp Arg Val Gly Gly Val Leu
    210                 215                 220

Ala Val Ser Arg Ala Phe Gly Asp Lys Leu Leu Lys Gln Tyr Val Val
225                 230                 235                 240

Ala Asp Pro Glu Ile Lys Glu Glu Val Val Asp Ser Ser Leu Glu Phe
                245                 250                 255

Leu Ile Leu Ala Ser Asp Gly Leu Trp Asp Val Val Thr Asn Glu Glu
            260                 265                 270

Ala Val Ala Met Val Lys Pro Ile Leu Asp Ser Glu Gln Ala Ala Lys
        275                 280                 285

Lys Leu Leu Gln Glu Ala Ser Gln Arg Gly Ser Ala Asp Asn Ile Thr
    290                 295                 300

Cys Leu Val Val Arg Phe Leu Glu Gln Glu Asn His Leu Pro Glu Arg
305                 310                 315                 320

Pro Thr Asn Asp Gln Ala Ser
                325

<210> SEQ ID NO 3
<211> LENGTH: 864
<212> TYPE: DNA
<213> ORGANISM: Oryza sativa

<400> SEQUENCE: 3
atggggctcg ccggagaggc cgctggctcg cctggcagtg gcggcgggtt cagtgcaaat      60
ggtaaattta gctatggtta tgcgagctct cctggaaaaa gatcctccat ggaggacttc     120
tatgacacca gaattgatgg tgtcgatgga gagaccgttg gactgtttgg tgtctttgat     180
ggtcatggtg gagctcgagc agcagaattc gtcaagcaga acctcttcac caatttaatc     240
aagcacccaa agttattcag tgataccaag tctgcaattg ctgaaactta cactagcacg     300
gactctgaac ttctgaaagc tgaaaccagc acaatcgag atgcagggtc gactgcctcc      360
actgcaattc tcgtaggcga ccgtctgctc gttgcaaatg ttggagattc tagggctgtc     420
atttgtagag gaggagatgc tatagctgtg tcaagagacc acaagcctga tcagtcagac     480
gagaggcaga ggatagagga tgctggtggt tttgtgatgt gggctggaac atggcgcgtg     540
ggtggtgttc ttgctgtctc tcgagcattt ggtgacaaac tcctgaagca atatgtggtt     600
gctgatccag agatcaagga ggaggtggtc gacagctctc tcgagttcct catccttgct     660
```

```
agtgatggcc tctgggacgt ggtgaccaac gaggaagctg tggccatggt gaagccaatt      720
ctggattcag agcaggctgc aaagaagctc ctccaggagg cctcacagag gggaagcgca      780
gacaacatca cctgcctcgt cgtccgtttc ttggagcagg agaatcacct gccagagaga      840
ccgacgaatg atcaagcctc ctaa                                             864
```

<210> SEQ ID NO 4
<211> LENGTH: 287
<212> TYPE: PRT
<213> ORGANISM: Oryza sativa

<400> SEQUENCE: 4

```
Met Gly Leu Ala Gly Glu Ala Ala Gly Ser Pro Gly Ser Gly Gly Gly
1               5                   10                  15

Phe Ser Ala Asn Gly Lys Phe Ser Tyr Gly Tyr Ala Ser Ser Pro Gly
            20                  25                  30

Lys Arg Ser Ser Met Glu Asp Phe Tyr Asp Thr Arg Ile Asp Gly Val
        35                  40                  45

Asp Gly Glu Thr Val Gly Leu Phe Gly Val Phe Asp Gly His Gly Gly
    50                  55                  60

Ala Arg Ala Ala Glu Phe Val Lys Gln Asn Leu Phe Thr Asn Leu Ile
65                  70                  75                  80

Lys His Pro Lys Leu Phe Ser Asp Thr Lys Ser Ala Ile Ala Glu Thr
                85                  90                  95

Tyr Thr Ser Thr Asp Ser Glu Leu Leu Lys Ala Glu Thr Ser His Asn
            100                 105                 110

Arg Asp Ala Gly Ser Thr Ala Ser Thr Ala Ile Leu Val Gly Asp Arg
        115                 120                 125

Leu Leu Val Ala Asn Val Gly Asp Ser Arg Ala Val Ile Cys Arg Gly
    130                 135                 140

Gly Asp Ala Ile Ala Val Ser Arg Asp His Lys Pro Asp Gln Ser Asp
145                 150                 155                 160

Glu Arg Gln Arg Ile Glu Asp Ala Gly Gly Phe Val Met Trp Ala Gly
                165                 170                 175

Thr Trp Arg Val Gly Gly Val Leu Ala Val Ser Arg Ala Phe Gly Asp
            180                 185                 190

Lys Leu Leu Lys Gln Tyr Val Val Ala Asp Pro Glu Ile Lys Glu Glu
        195                 200                 205

Val Val Asp Ser Ser Leu Glu Phe Leu Ile Leu Ala Ser Asp Gly Leu
    210                 215                 220

Trp Asp Val Val Thr Asn Glu Glu Ala Val Ala Met Val Lys Pro Ile
225                 230                 235                 240

Leu Asp Ser Glu Gln Ala Ala Lys Lys Leu Leu Gln Glu Ala Ser Gln
                245                 250                 255

Arg Gly Ser Ala Asp Asn Ile Thr Cys Leu Val Val Arg Phe Leu Glu
            260                 265                 270

Gln Glu Asn His Leu Pro Glu Arg Pro Thr Asn Asp Gln Ala Ser
        275                 280                 285
```

<210> SEQ ID NO 5
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 5
gatggagaga ccgttggact gtttg                                          25

<210> SEQ ID NO 6
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 6
gattgaggac caacacttaa cctgc                                          25

<210> SEQ ID NO 7
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 7
gaacattcat gatacagacc aggac                                          25

<210> SEQ ID NO 8
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 8
cctgcatctc gattgtggct ggttt                                          25

<210> SEQ ID NO 9
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 9
accaacgctg atcaattcca cag                                            23

<210> SEQ ID NO 10
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 10
actgatagtt taaactgaag gcgg                                           24

<210> SEQ ID NO 11
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 11
caagctttcc gacttctgag tcggtggcga gtac                                34

<210> SEQ ID NO 12
<211> LENGTH: 40
<212> TYPE: DNA

<213> ORGANISM: Artificial Sequence
<220> FEATURE:
<223> OTHER INFORMATION: Synthetic Polynucleotide

<400> SEQUENCE: 12
cactagtcag atctaccatg cacgcgaacg acggaggagg                                40

<210> SEQ ID NO 13
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 13
gcgactagtc tctcgcaggg agcgga                                              26

<210> SEQ ID NO 14
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 14
gcgaagcttt taggaggctt gatcattcgt cggtc                                    35

<210> SEQ ID NO 15
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 15
gcgactagtg acgaagtttc tcctgcagtc gctgttcc                                 38

<210> SEQ ID NO 16
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 16
gcgaagcttt caattcaagg atttgctctt gaatttcc                                 38

<210> SEQ ID NO 17
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 17
gctggtcatg gtggagctcg agcagcagaa ttcgtc                                   36

<210> SEQ ID NO 18
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 18
aaagacacca aacagtccaa cggtctctcc atc                                      33

<210> SEQ ID NO 19
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 19
cgcggccgca ccatgcgtga ggtgctcctc ctcg                               34

<210> SEQ ID NO 20
<211> LENGTH: 92
<212> TYPE: DNA
<213> ORGANISM: Artificial Sequence
<220> FEATURE:
<223> OTHER INFORMATION: Synthetic Polynucleotide

<400> SEQUENCE: 20
cgcactagtt caagcgtagt ctggaacgtc gtatgggtaa ccagcgtagt ctggaacgtc    60
gtatgggtaa ggggaggctt gatcattcgt cg                                 92

<210> SEQ ID NO 21
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 21
gctgggctcg ccggagagg                                                19

<210> SEQ ID NO 22
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 22
caagcgcacc tcgccgtcgt                                               20

<210> SEQ ID NO 23
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 23
atggggctcg ccggagagg                                                19

<210> SEQ ID NO 24
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 24
ggtgcggccg cgtcaagagt ccccccgtgtt c                                 31

<210> SEQ ID NO 25
<211> LENGTH: 28
<212> TYPE: DNA

<213> ORGANISM: Artificial Sequence
<220> FEATURE:
<223> OTHER INFORMATION: Synthetic Polynucleotide

<400> SEQUENCE: 25
ctcacctatg gtgttcaatg cttttcaa                                           28

<210> SEQ ID NO 26
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 26
agtagtgaca agtgttggcc acggaa                                             26

<210> SEQ ID NO 27
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 27
cgccaattgg tcattcatat gcttgagaag agagtcg                                 37

<210> SEQ ID NO 28
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 28
cgcggtaccc ttctacctac aaaaaagctc cgcacg                                  36

<210> SEQ ID NO 29
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 29
cgcggtacca tgaaagcgtt aacggccagg c                                       31

<210> SEQ ID NO 30
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 30
cgcactagtg tttgggatgt tttactcctc atatta                                  36

<210> SEQ ID NO 31
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 31
cgctctagac agcttgggct gcaggtcgag gc                                      32

<210> SEQ ID NO 32
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 32
cgcgcggccg cctcgaggct agagtcgact agcttcag                        38

<210> SEQ ID NO 33
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 33
caagaggtga cgatggagat ga                                          22

<210> SEQ ID NO 34
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 34
cgtagaccga ccagattaag agtaga                                      26

<210> SEQ ID NO 35
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 35
tggcactgta acacatgatt cg                                          22

<210> SEQ ID NO 36
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 36
tcttcttact tgtcttgtct ctgtaattac tg                               32

<210> SEQ ID NO 37
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 37
aaaaaggaaa aaaaaatgag gggaca                                      26

<210> SEQ ID NO 38
<211> LENGTH: 27
<212> TYPE: DNA
<213> ORGANISM: Artificial Sequence
<220> FEATURE:

<223> OTHER INFORMATION: Synthetic Polynucleotide

<400> SEQUENCE: 38
caccagcttt gtgcttttga tgatcta          27

<210> SEQ ID NO 39
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 39
ccaaagataa taaaagcaga gacatga          27

<210> SEQ ID NO 40
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 40
taagccgccg ccaaaat          17

<210> SEQ ID NO 41
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 41
cgtccagctc cccgaaat          18

<210> SEQ ID NO 42
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 42
tagggtcgtt gtacgtcgtt tatc          24

<210> SEQ ID NO 43
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 43
tgcgatgccg gttaaggt          18

<210> SEQ ID NO 44
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 44
tggctcataa accgacttgc taa          23

<210> SEQ ID NO 45
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 45
acagcaccaa cgcacgcaag atgat                                    25

<210> SEQ ID NO 46
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 46
gtgaacggcg gcgacggagc                                          20

<210> SEQ ID NO 47
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 47
cgaggtcagg aaagtctgct ccaag                                    25

<210> SEQ ID NO 48
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 48
ctgtcccagc aagatgcaca tgaac                                    25

<210> SEQ ID NO 49
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 49
tccagtagtg caaacgcaca tt                                       22

<210> SEQ ID NO 50
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 50
aagaaattaa gggagatgtt gcaaac                                   26

<210> SEQ ID NO 51
<211> LENGTH: 21
<212> TYPE: DNA
<213> ORGANISM: Artificial Sequence
<220> FEATURE:
<223> OTHER INFORMATION: Synthetic Polynucleotide

```
<400> SEQUENCE: 51
gccgtgaatg atttcccttt g                                              21

<210> SEQ ID NO 52
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 52
cacacccgtc agaaatcctc c                                              21
```

TRANSGENIC PLANTS EXPRESSING TYPE 2C PROTEIN PHOSPHATASE ABSCISIC ACID (PP2CABA) PROTEINS AND USES THEREOF

RELATED APPLICATION

The present application claims priority under 35 U.S.C. § 119(e) to U.S. Provisional Application No. 62/433,212 filed on Dec. 12, 2016, the entire content of which is incorporated by reference herein.

FIELD OF TECHNOLOGY

The present disclosure relates to the use of a PP2CABA protein for enhancing features of transgenic plants overly expressing such.

BACKGROUND OF THE INVENTION

Plants have developed various strategies and mechanisms, including anatomical and physiological adaptations, to survive unfavorable environmental stresses. Roots are one of the most sensitive organs sensing the changing environments, as they are in direct contact with soils which may vary in water content and composition of nutrients and microorganisms constantly. Hence, plant root architecture is essential for water and nutrient uptake, anchorage to soil, and interaction with soil microorganisms, functions that impact growth, biotic and abiotic stress tolerance, and yield. The development of root architecture can be controlled by abiotic stresses including drought, salinity, flooding and nutrients in soil and soil matrix heterogeneity, and such root developmental plasticity offers one of the major acclimation strategies for plants to adapt to changing environments in the soil is of great agronomic importance (Lopez-Bucio et al., Curr Opin Plant Biol, 6:280 (2003); Malamy, Plant Cell Environ, 28:67 (2005); Potters et al., Trends Plant Sci, 12:98, (2007); Robbins et al., J Exp Bot, 66:2145 (2015)). For examples, the majority of drought-resistant rice varieties have a deeper and more highly branched root system than drought sensitive varieties (Price et al., Theor Appl Genet, 95:132 (1997); Uga et al., Nat Genet, 45:1097 (2013)). In contrast, arrest of root growth for conservation of resources under severe drought stress until recovery by rehydration is essential for maize roots to survive throughout the stress period Stasovski et al., Can J Bot, 69:1170 (1991)). Consequently, investigation on detailed mechanisms underlying regulation of root architecture by environmental cues, and the function of root system developed under different stress conditions, are not only interesting from a basic research standpoint, but also crucial in improving water use efficiency and stress tolerance in crops.

Root systems include primary roots (PRs) and lateral roots (LRs) that originated from PRs. LR formation is pre-initiated from pericycle cells in the basal meristem close to root tip, and lateral root primordium (LRP) formation occurs higher up in the maturation zone of the root (De Smet et al., Development, 134:681 (2007); Dubrov sky et al., Plant Physiol, 124:1648 (2000)). The LRP is initiated deep within PR, making it necessary that root primordium breaks and extends through the overlying tissues to merge to the root surface. Arabidopsis has a very simple root anatomy, with the stele being surrounded by one layer each of pericycle, endodermis, cortex and epidermis; whereas, in rice, the pericycle is surrounded by the endodermis, cortex, sclerenchyma, exodermis and epidermis, and these tissues are composed of up to 20 layers of cells, making the emergence of LRP a challenging process (Peret et al., J Exp Bot, 60:3637 (2009b)).

The development of two protective sheaths, endodermis and exodermis, play important roles in basic root function and protection against stresses such as drought, pathogens, organic contaminants, heavy metals and salinity (Enstone et al., J Plant Growth Regul, 21:335 (2003a); Moura et al., J Integr Plant Biol, 52:360 (2010)). Cell walls of these two tissues are thickened by suberization and connected by Casparian strips that are mainly made of lignin and with lower amount of suberin. The endodermis Casparian strip blocks the passive flow of materials such as water and solutes into the stele, and the exodermis Casparian strip protects roots against pathogen invasion from soil, filters ions from the soil solution, and prevents root drying under limited water supply in soil (Enstone et al., J Plant Growth Regul 21:335 (2003a)). Cell walls of the peripheral sclerenchyma in roots are also thickened with liginification. These structurally specialized tissues provide mechanical strength, rigidity and hydrophobicity that allow plants to stand upright, withstand the pressure of water transport, and maintain a constant clean water status required for terrestrial life (Enstone et al., J Plant Growth Regul, 21:335 (2003a); Rogers et al., New Phytol, 164:17 (2004)).

Lignin and suberin are synthesized in specialized tissues not only during the development but also in response to environmental stimuli such as exposure to abiotic stresses, such as drought, cold, salinity, heavy metals, and anoxia, in roots (Cabane et al., Biosynthesis, Biodegradation and Bioengineering, 61:219 (2012); Enstone et al., J Plant Growth Regul, 21:335 (2003a); Moura et al., J Integr Plant Biol, 52:360 (2010); Ranathunge et al., Plant Science, 180:399 (2011)). The most common stress experienced by roots is water stress that may lead to collapse of tissues and loss of water. Maize seedling seminal roots develop extensive suberization in both the endodermis and exodermal layers under soil drying conditions, and since lignin and suberin are both composed of hydrophobic polymers, the two tissues could serve as barriers to water loss and protect root tips alive throughout the drought stress period (Stasovski et al., Can J Bot, 69:1170 (1991)).

Plants have developed sensing and signal transduction systems in response to water limitation in soil. Reversible protein phosphorylation mediated by kinases and protein phosphatases is part of the system controlling the adaptive cellular response to maintain a balance of growth under normal and adverse environmental conditions. Accumulation of the stress hormone abscisic acid (ABA) is one of the outputs of upstream sensing and signaling in response to drought and other abiotic stresses as well as a key regulator of downstream responses (Cutler et al., Annu Rev Plant Biol, 61:651 (2010)). Type 2C protein phosphatases (PP2Cs) are composed of a superfamily of 80 putative members in Arabidopsis and 90 in rice, and that could be classified into 10-13 clades (Fuchs et al., The FEBS journal, 280:681 (2013); Singh et al., BMC Genomics, 11:435 (2010); Xue et al., BMC Genomics, 9:550 (2008)). In Arabidopsis, Glade-A PP2Cs have been most extensively studied, and at least seven of the nine PP2Cs in this group negatively regulate the ABA-invoked physiological responses, such as the inhibition of germination and root growth or stomata closure (Fuchs et al., The FEBS journal, 280:681 (2013)). Under normal growth conditions, in which cellular ABA levels are low, group-A PP2Cs interact with the downstream target, sucrose nonfermenting-related protein kinases group 2 (SnRK2s). Under osmotic stress conditions, such as drought and high salinity, ABA is perceived by PYR/PYL/RCAR receptors that inhibit the phosphatase activities of PP2Cs, which enable the activation of SnRK2s and result in the phosphorylation of downstream substrates and gene expression (Cutler et al., Annu Rev Plant Biol, 61:651 (2010); Fuchs et al., The FEBS journal, 280:681 (2013); Yoshida et al., Plant Cell Physiol, 56:1043 (2015)).

Water is fundamental to plant life, but the mechanisms by which plant roots sense and respond to variations in water availability in the soil are poorly understood. Sensitive responses are necessary for optimal functionality of the root system in a heterogeneous moisture environment, allowing for efficient water uptake with minimal water loss during periods of drought (Robbins et al., J Exp Bot, 66:2145 (2015)). There is therefore a need to develop new strategies for generating plants that have enhanced tolerance to multiple stresses while maintaining desired traits such as high yield, with minimal or no unfavorable adverse effects.

BRIEF SUMMARY OF THE INVENTION

The present disclosure is based, at least in part, on the unexpected findings that expression of a type 2C protein phosphatase abscisic acid (PP2CABA) resulted in improved osmotic stress tolerance and/or root architecture in transgenic plants overly expressing such. As disclosed herein, PP2CABA expression unexpectedly promoted prevention of excess water loss when the transgenic plant is grown or maintained under deficit conditions. Furthermore, PP2CABA primed the transgenic plants recovered more rapidly and continued to grow normally following application of osmotic stress, when compared to control plant of the same genetic background but which was not primed.

Accordingly, one aspect of the present disclosure features a vector comprising a nucleic acid operably linked to a promoter, wherein the nucleic acid encodes a type 2C protein phosphatase abscisic acid (PP2CABA) protein. In some embodiments, the promoter is heterologous to a naturally occurring gene encoding the PP2CABA protein. In some examples, the nucleic acid encoding the PP2CABA protein as described herein is derived from a different kingdom, family, or species as the promoter.

Any of the PP2CABA proteins described herein may comprise an amino acid sequence at least 85% (e.g., 90%, 95%, 96%, 97%, 98% or 99%) identical to SEQ ID NO: 4. In one example, the PP2CABA protein comprises the amino acid sequence of SEQ ID NO: 4. Any of the PP2CABA proteins described herein may comprise an amino acid sequence at least 85% (e.g., 90%, 95%, 96%, 97%, 98% or 99%) identical to SEQ ID NO: 2. In one example, the proteins described herein comprises the amino acid sequence of SEQ ID NO: 2.

The promoter for use in any of the vectors described herein may be a constitutive promoter, a tissue-specific promoter, a developmental stage-specific promoter, or a promoter inducible by biotic or abiotic stress. Exemplary constitutive promoters include, but are not limited to, a maize ubiquitin (Ubi) promoter, a rice actin (ActI) promoter, and a cauliflower mosaic virus 35S (CaMV35S) promoter. Exemplary tissue-specific promoters include, but are not limited to, a rice glutelin (GluB) promoter, a rubisco small subunit (rbcS) promoter, and a maize zean gene promoter. Exemplary developmental stage-specific promoters include, but are not limited to, a rice alpha-amylase (α-Amy) promoter, and a rice glycine rich RNA binding protein (GRRP-A1) promoter. Exemplary promoters inducible by biotic or abiotic stress include, but are not limited to, an *Arabidopsis* rd29A promoter, an *Arabidopsis* corl SA promoter, an *Arabidopsis* kin1 promoter, an *Arabidopsis* heat-shock factor (HSF) promoter, an *Arabidopsis* C-repeat-binding factor (CBF1) promoter, an *Arabidopsis* dehydration-responsive element binding protein (DREB1A) promoter, a rice HVA1 promoter, a rice HVA22 promoter, a rice PP2CABA promoter, an alcohol dehydrogenase (Adh) promoter, an ethanol-inducible promoter, an alpha-amylase promoter, and a synthetic ABRC321 promoter. The inducible promoter may be triggered by one or more of drought, salt, high or low temperatures, hypoxia, anoxia, hydration, pH, chemicals, and/or hormones.

In another aspect, the present disclosure also provides an isolated host cell comprising any of the vectors described herein. In some embodiments, the isolated host cell can be a plant host cell or an *Agrobacterium* host cell. For example, a plant host cell can be a cell of a monocot plant, e.g., maize, wheat, barley, millet, sugarcane, rice, miscanthus, switchgrass or sorghum. In other examples, the plant host cell can be a cell from a dicot plant, e.g., *Arabidopsis*, soybean, oilseed *Brassica*, peanut, sunflower, safflower, cotton, tobacco, tomato, pea, chickpea, pigeon pea, potato, or cocoa.

In another aspect, the present disclosure features a transgenic plant, comprising an exogenous nucleic acid operably linked to a promoter as described herein. The exogenous nucleic acid encodes any of the type 2C protein phosphatase abscisic acid (PP2CABA) proteins disclosed herein. In some embodiments, the promoter operably linked to the exogenous nucleic acid in the transgenic plant is heterologous to a naturally occurring gene encoding the PP2CABA protein.

In some examples, the transgenic plant disclosed herein exhibits a lower lateral roots (LR) to primary roots (PR) ratio, a larger root diameter, a higher tolerance to abiotic stress, increased levels of lignin and/or suberin, or a combination thereof as compared with a non-transgenic plant counterpart growing under the same conditions.

In some embodiments, the transgenic plant can be a monocot plant. Examples include, but are not limited to, maize, wheat, barley, millet, sugarcane, rice, miscanthus, switchgrass or sorghum. In other embodiments, the transgenic plant can be a dicot plant. Examples include, but are not limited to, *Arabidopsis*, soybean, oilseed *Brassica*, peanut, sunflower, safflower, cotton, tobacco, tomato, pea, chickpea, pigeon pea, potato, or cocoa.

Also within the scope of the present disclosure are methods of producing the transgenic plants described herein. The method may comprise: (a) transforming a plant cell with a nucleic acid operably linked to a promoter to obtain a recombinant plant cell expressing a PP2CABA protein, wherein the nucleic acid encodes the PP2CABA protein; and (b) growing the recombinant plant cell obtained in (a) to generate the transgenic plant.

Further the present disclosure provides methods for improving growth (e.g., under stress and/or during recovery from stress), stress tolerance, and/or root architecture of a plant. The method may comprise: (a) transforming plant cells with a nucleic acid operably linked to a promoter to obtain recombinant plant cells expressing a PP2CABA protein, wherein the nucleic acid encodes the PP2CABA protein; (b) growing the recombinant plant cells obtained in (a) to generate a plurality of transgenic plants; and (c) selecting a transgenic plant from the plurality of transgenic plants generated in (b) that exhibits a lower lateral roots (LR) to primary roots (PR) ratio, a larger root diameter, increased levels of lignin and/or suberin, a higher tolerance to abiotic stress, or a combination thereof, as compared with a non-transgenic plant counterpart growing under the same conditions. In some embodiments, abiotic stress comprises osmotic stress, drought stress, salt stress, or a combination thereof.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

The foregoing summary, as well as the following detailed description of the disclosure, will be better understood when read in conjunction with the appended drawings. For the purpose of illustrating the disclosure, they are shown in the drawings embodiments which are presently preferred. It should be understood, however, that the disclosure is not limited to the precise arrangements and instrumentalities shown.

In the drawings:

FIG. 3A shows PP2CABA promoter activity in response to ABA and abiotic stress. Ten-day-old rice seedlings were treated with 5 μM ABA, 200 mM NaCl, dehydration on tissue papers, or 4° C. for 3 hours. Total RNAs were purified from shoots and roots, and subjected to quantitative RT-PCR analysis using gene specific primers. FIG. 3B shows dose-dependent induction of PP2CABA by ABA. Ten-day-old WT rice seedlings were treated with various concentrations of ABA for 24 hours. Total RNAs were purified from roots, and subjected to quantitative RT-PCR analysis using PP2CABA-specific primers. FIG. 3C shows PP2CABA is an active protein phosphatase in vitro. Recombinant GST-PP2CABA, GST-PP2CABA (D100A), GST-ABI2, and GST proteins were expressed in *E. coli*, purified and reacted with a phosphor peptide substrate, RRApTVA, and phosphatase activities were determined by measuring released free phosphate. FIG. 3D shows tissues-specific PP2CABA promoter activity in response to ABA. Ten-day-old seedlings of transgenic rice carrying PP2CABA:GUS were treated with (lower panel) or without (upper panel) 10 μM ABA for 1 day and then stained for GUS activity. Arrow indicates young leaves.

FIG. 4A includes a diagram showing the gene structure and T-DNA insertion site in PP2CABA. Gray box indicates exon, line indicates intron, white box indicates 5'- and 3'-untranslated regions and triangle indicates T-DNA which is inserted PP2CABA in the pp2caba mutant. Bold arrow on T-DNA indicates position and orientation of the CaMV35S enhancer (35SE) octamer and GUS. ATG indicates the translation initiation codon. Arrowheads indicate positions of DNA primers used for genotyping and RT-PCR analyses. FIG. 4B shows genotyping of pp2caba. PCR with DNA primers 2C1 and 2C3 produced a product of 637 bp from wild-type (WT) rice genomic DNA, and with DNA primers GUS2 and 2C1 produced a product of 528 bp from the rice genomic DNA-T-DNA junction region, and with DNA primers RBSP and GUS2 produced a product of 335 bp from T-DNA in the pp2caba. +/+, WT; +/−, heterozygous (He) mutant; −/−, homozygous (Ho) mutant. FIG. 4C shows PP2CABA has been knocked out in pp2caba. Ten-day-old seedlings from WT or Ho mutant were treated with or without 10 μM ABA for 24 h. Total RNAs were purified from roots, and subjected to RT-PCR analysis using primers specific for indicated genes.

FIG. 5A shows loss-of-function analysis. Ten-day-old seedlings of segregated wild type (WT) or pp2caba homozygous mutant were treated with (+) or without (−) 1 μM ABA for 3 days. Upper panel: morphology of roots. Lower panel: elongation of LR in boxed area (1 cm above the root tip) of roots in upper panel. LRP (marked by arrowheads) were initiated but not elongated in WT in the presence of ABA. FIG. 5B shows two-day-old seedlings of WT and transgenic rice carrying XVE:PP2CABA were treated with or without 1 μM β-Estradiol for 8 days. Upper panel: morphology of roots. Lower panel: elongation of LR in boxed area (2 cm above the root tip) of roots in upper panel. LRP (marked by arrowheads) were initiated but not elongated in PP2CABA-overexpressing transgenic rice. S: seminal roots. C: crown roots.

FIG. 6A to FIG. 6E include diagrams showing PP2CABA having two forms which are translated from the first and the second ATG codons. FIG. 6A shows that the cDNA of PP2CABA contains two putative translation initiation codon ATGs. The 2nd ATG encodes the Met at amino acid residue 41. Amino acids 1-24 are putative signal peptide (SP). FIG. 6B shows total cellular proteins were extracted from dry embryos of WT and pp2caba and subjected to Western blot analysis using anti-PP2CABA antibodies (upper panel). Protein loading is shown by the Ponceau S staining (lower panel). Molecular weights of L and S forms of PP2CABA are shown on the right-hand side. FIG. 6C shows the total cellular proteins were extracted from rice protoplasts transient transfected with 35S:PP2CABA1-dHA, 35S:PP2CABA1 (M41A)-dHA or 35S:PP2CABA1 (25-327)-dHA and subjected to Western blot analysis using anti-HA antibodies (upper panel). Protein loading control is shown by the Coomassie blue staining (lower panel). Amino acid residue Met at position 41 was replaced with Ala, so that protein translation was not initiated from this internal Met. FIG. 6D shows that the recombinant GST-PP2CABA(25-327), GST-PPCABA(41-327), and GST proteins were expressed in *E. coli*, purified and reacted with a phosphor peptide substrate, RRApTVA, and phosphatase activities were determined by measuring released free phosphate. FIG. 6E shows that the rice protoplasts were transfected with constructs 35S:GFP, 35S:PP2CABA-GFP, 35S:PP2CABA (M41A)-GFP or 35S:PP2CABA (41-327)-GFP, and the GFP signal was examined under a confocal microscope. Amino acid residue Met at position 41 was replaced with Ala, so that protein translation was not initiated from this internal Met.

FIG. 7A shows two-day-old seedlings of WT and transgenic rice carrying XVE:PP2CABA-dHA, XVE:PP2CABA (M41A)-dHA or XVE:PP2CABA (41-327)-dHA were treated with 1 µM β-Estradiol for 8 days. Protein levels of PP2CABA were detected in roots of wild-type and transgenic plants by western blot analysis using anti-HA antibodies (upper panel). Protein loading is shown by the Ponceau S staining (lower panel). FIG. 7B shows root morphology of seedlings in FIG. 7A was recorded photographically.

FIG. 8A shows fold change and relative mRNA levels of PP2CABA up-regulated genes essential for phenylpropanoid biosynthesis, fatty acid elongation and lipid transfer. FIG. 8B shows metabolic pathways for biosynthesis of lignin and suberin polymers. PP2CABA up-regulated genes (including PAL, CCR, CAD, POX, LTP, and KCS) are shown in italicized font.

FIG. 9A shows two-day-old seedlings of transgenic rice lines XVE:PP2CABA-dHA and WT transferred to Yoshida solution with (+) or without (−) 1 µM β-Estradiol for 8 days. FIG. 9B shows two-day-old WT seedlings grown in Yoshida solution for 8 days, then treated with various concentrations of ABA for 24 hours. Total RNA was purified from roots and subjected to quantitative RT-PCR analysis using gene specific primers.

FIG. 10A shows two-day-old seedlings of WT and pp2caba grown in Yoshida solution for 8 days. 1 µM ABA was added and seedlings were cultured for another 3 days. FIG. 10B shows two-day-old seedlings of transgenic rice line XVE:PP2CABA-dHA and WT transferred to Yoshida phytagel with or without 1 µM β-Estradiol for 8 days. Roots at 1 cm above the apex were cross-sectioned and stained with acriflavine for lignin and fluorol yellow 088 for suberin. F, fluorescence image; T, transmission image; EP, epidermis; EX, exodermis; SC, sclerenchyma; CO, cortex. Scale bars=10 µm.

FIG. 12A shows two-day-old seedlings of transgenic rice line XVE:PP2CABA-dHA and WT were transferred to hydroponic solution with or without 1 µM β-estradiol for 8 days. β-Estradiol were then removed and plants were treated with or without 20% PEG6000 for 7-days and recovered in hydroponic solution for 5-days. Morphology of plants are shown. Arrow indicates PP2CABA-primed seedlings. FIG. 12B shows morphology of roots of plants during the treatment with PEG in FIG. 12A. Horizontal dotted line and horizontal long dashed line indicate starting and end points of root growth, respectively, during PEG treatment. FIG. 12C shows five-day-old seedlings of transgenic rice line XVE:PP2CABA-dHA and WT transferred to vermiculite and treated with or without 1 µM β-estradiol for 11 days. Plants were dehydrated for 15 days without water, and then recovered by watered with hydroponic solution for 10 days.

DETAILED DESCRIPTION OF THE INVENTION

Figure 1:
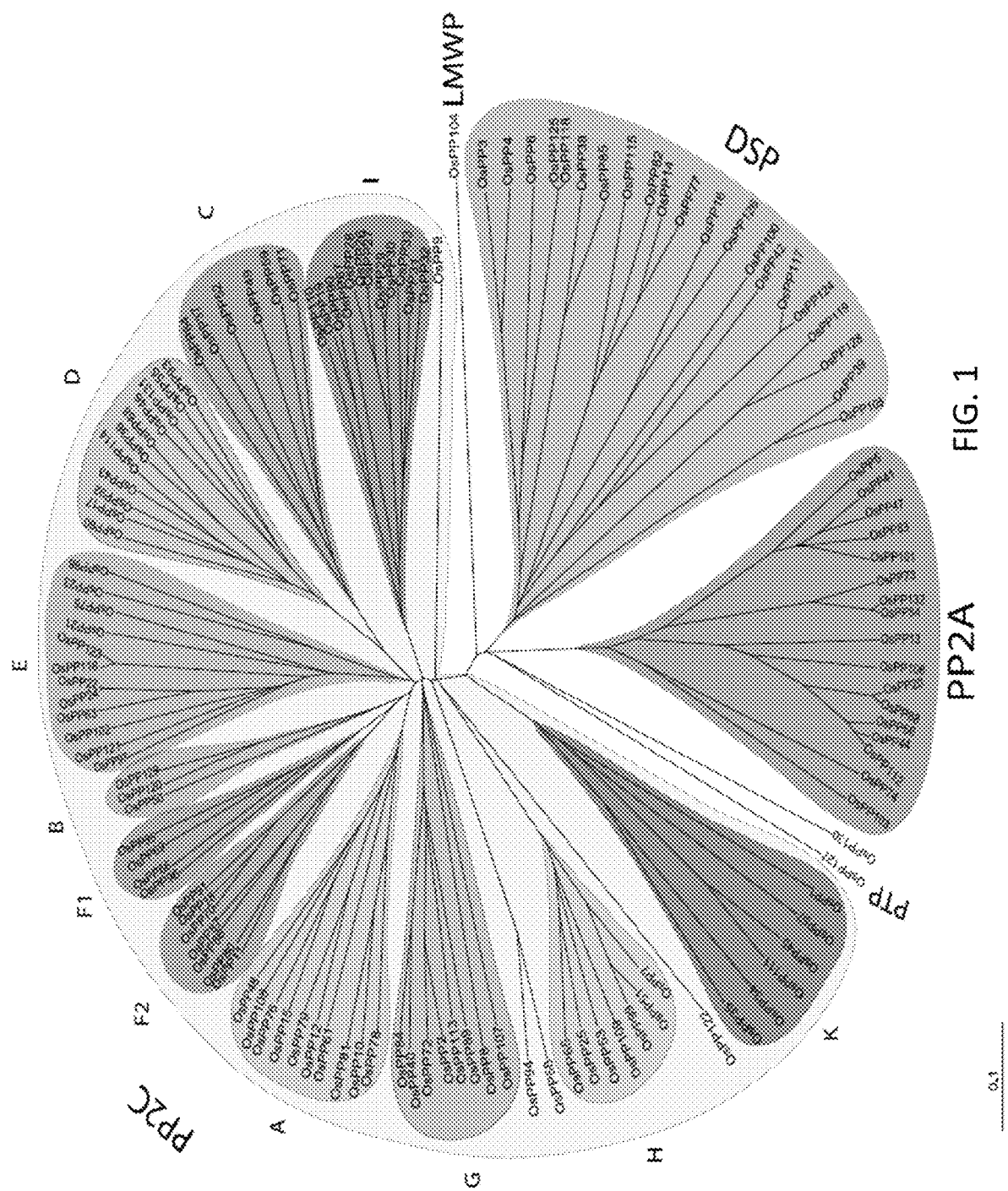
FIG. 1 is a diagram showing phylogenetic analysis of protein phosphatase genes in the rice genome. There are a total of 132 protein phosphatase genes in the rice genome (Singh et al., BMC Genomics, 11:435 (2010)). Among these protein phosphatase genes, 90 belong to class PP2C. PP2CABA/OsPP91 belongs to Group-F2 PP2C.

The present studies revealed that, unexpectedly, PP2CABA proteins improved features of transgenic plants overly expressing such, for example growth properties and/or stress tolerance. Accordingly, provided herein are transgenic plants overly expressing a PP2CABA as described herein, vectors for expressing the PP2CABA protein, methods for making the transgenic plants, and methods for improving growth properties or stress tolerance of plants by over-expressing a PP2CABA protein.

I. PP2CABA Protein

Type 2C protein phosphatase abscisic acid (PP2CABA) is a phosphatase found in various plant species. The present studies revealed that this protein may be involved in abscisic acid (ABA) signaling and stress response. P2CABA has two forms, a long (L) form and a short (S) form. As also demonstrated herein, PP2CABA unexpectedly promoted lignification and suberization in cell walls of periphery root tissues by enhancing the expression of genes involved in these processes (e.g., upregulation of genes including but not limited to SWN1, SWN2, MYB96, CCR, KCS, LTP, POX and LEA3), leading to inhibition of lateral root emergence and enlargement of root diameter under ABA treatment and osmotic stress. These modifications were associated with prevention of excess water loss when the plant is grown or maintained under water deficit conditions. In addition, priming of plants by transient expression of PP2CABA promoted the acclimation of plants to osmotic stress; PP2CABA-primed plants recovered more rapidly and continued to grow normally following said application of osmotic stress, when compared to control plant of the same genetic background but which was not primed. As such, the studies described herein have revealed an advantageous adaptive mechanism in plants to promote abiotic stress tolerance, through the expression of PP2CABA in said plants. See Examples below.

According to the present disclosure, the terms "polypeptide," "peptide" and "protein" as used herein refer to a polymer formed of amino acid residues, wherein one or more amino acid residues are naturally occurring amino acids or artificial chemical mimics.

The PP2CABA protein described herein can be a naturally occurring protein of any suitable species. Exemplary PP2CABA protein sequences may be from plants including, but not limited to *Orzya sativa* Japonica Group (e.g., under GenBank accession number BAF20378), *Sorghum bicolor* (e.g., under GenBank accession number XP_021304510) and *Setaria Italica* (e.g., under GenBank accession number XP_004966135). Additional exemplary PP2CABA proteins include but are not limited to those listed under accession numbers EMS67352, XP 015626502 and XP 015626501.

In some embodiments, the PP2CABA protein may comprise the amino acid sequence of SEQ ID NO:2 or SEQ ID NO:4. Alternatively, the PP2CABA protein may be a naturally occurring protein that is highly homologous to SEQ ID NO:2 or SEQ ID NO:4, for example, sharing at least 85% sequence identity in the entire length (e.g., at least 90%, at least 93%, at least 95%, or at least 97%). Such PP2CABA proteins can be readily identified from publically available gene database (e.g., GenBank) using SEQ ID NO:2 or SEQ ID NO:4 as a query.

The "percent identity" of two amino acid sequences may be determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, word-length=3 to obtain amino acid sequences homologous to the protein molecules of the disclosure. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

In some embodiments, the PP2CABA protein can be a functional variant of a naturally occurring PP2CABA protein. Such a functional variant may share a high sequence identity with the wild-type counterpart, for example, at least 85% (e.g., 90%, 95%, 96%, 97%, 98% or 99%) to the amino acid sequence of the wild-type counterpart and possess substantially similar bioactivities as the wild-type counterpart.

In some examples, the functional variant may include only conservative amino acid substitutions relative to the wild-type counterpart. The skilled artisan will realize that conservative amino acid substitutions may be made in a PP2CABA protein to provide functionally equivalent variants, i.e., the variants retain the functional capabilities of the particular wild-type PP2CABA. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

The functionality of a particular PP2CABA protein may be confirmed by any suitable assay method known in the art or those described herein, for example, the phosphatase assay described in the Examples section below.

II. Vectors Encoding PP2CABA Proteins

Also provided herein, in some aspects, are vectors comprising a nucleic acid encoding any of the PP2CABA proteins described herein. The term "nucleic acid" as used herein refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either stranded form, or a double-stranded helix.

A "vector," as used herein, can be a recombinant nucleic acid-based vehicle to artificially carry foreign genetic material into a host cell, in which the foreign genetic material can be replicated and/or expressed. The vector as described herein may be a cloning and/or an expression vector. In some embodiments, the vector can be a viral vector or a non-viral vector (e.g., a plasmid). In particularly examples, the vectors may be plant vectors or *Agrobacterium* vectors.

A nucleic acid "encoding" or "coding for" a protein means that the nucleic acid can produce the protein through the transcription and translation process in a host cell or in a cell-free system, following the rule of the genetic code, which is the relation between the sequence of bases in DNA and the sequence of amino-acids in proteins. In some instances, the nucleic acids coding for the PP2CABA protein as described herein may subject to codon optimization in light of the host cell, in which the protein is to be expressed.

In some instances, the nucleic acid disclosed herein may further comprise one or more untranslated regions (UTR) in addition to the coding sequence. As used herein, UTR refers to nucleotide sequences encompassing the non-protein-coding region of an mRNA molecule. These untranslated regions can reside at the 5' end (5' UTR) or the 3' end (3' UTR) an mRNA molecule.

In some embodiments, the nucleic acid encoding the PP2CABA protein can be operably linked to a promoter in the vector to drive expression of the PP2CABA protein either in vitro or in vivo. The vector may be in linear or circular form. It may remain episomal or integrate into the host cell genome when introduced into a host cell.

In some embodiments, the vector described herein is suitable for expressing the encoded PP2CABA protein in a prokaryote cell. In addition to a suitable promoter, such a vector may also comprise an operator (optional), and a ribosome binding site, and other suitable sequences as known in the art. Promoters suitable for driving protein expression in prokaryote cells are well known in the art.

In other embodiments, the vector described herein is suitable for expressing the encoded PP2CABA protein in a Eukaryotic cell. In addition to a suitable promoter, other nucleic acid sequences which may be needed for this purpose include, but are not limited to, enhancers, termination and polyadenylation signals, and other suitable sequences as known in the art. It is not intended that the present disclosure be limited to particular cloning/expression vectors or cloning/expression vectors with particular elements.

In some embodiments, the vector described herein can be a viral vector. Suitable viral vectors include double-stranded DNA from a virus having a double stranded DNA genome or replication intermediate. The excised viral DNA is capable of acting as a replicon or replication intermediate, either independently, or with factors supplied in trans. The viral DNA may or may not encode infectious viral particles and furthermore may contain insertions, deletions, substitutions, rearrangements or other modifications. The viral DNA may contain heterologous DNA, which is any non-viral DNA or DNA from a different virus. For example, the heterologous DNA may comprise an expression cassette for a protein or RNA of interest (e.g., a PP2CABA protein or PP2CABA RNA).

Super binary vectors carrying the vir genes of *Agrobacterium* strains A281 and A348 may be useful for high efficiency transformation of monocots. Alternatively, T-DNA may be used to transfer nucleic acids for expressing the PP2CABA protein as described herein to maize at a suitable efficiency, e.g., resulting in systemic infection by viruses introduced by agroinfection but not tumor formation. (Grimsley et al., (1989) Mol. Gen. Genet. 217:309-316).

Promoter, as described herein, refers to a nucleotide sequence (site) on a DNA molecule to which RNA polymerase can bind to initiate the transcription of the coding DNA into mRNA, which will then be translated into the corresponding protein (i.e., expression of a gene). A promoter is considered to be "operably linked" to a coding sequence when it is in a correct functional location and orientation in relation to the coding sequence to control ("drive") transcriptional initiation and expression of that the coding sequence (to produce the corresponding protein molecules). In some instances, the promoter described herein can be constitutive, which initiates transcription independent of the influence of regulation. Exemplary constitutive promoters include, but are not limited to a maize ubiquitin (Ubi) promoter, a rice actin (Act1) promoter, and a cauliflower mosaic virus 35S (CaMV35S) promoter.

In other instances, the promoter described herein can be inducible, which initiates transcription in a regulated manner, for example, in the presence or absence of a particular factor. Exemplary inducible promoters include an ethanol inducible promoter (e.g., a A1cR/A1cA promoter) or a β-estradiol inducible promoter (e.g., a XVE promoter, see Examples section below).

Exemplary tissue-specific promoters include a rice glutelin (GluB) promoter, a rubisco small subunit (rbcS) promoter, and a maize zean gene promoter.

Exemplary developmental stage-specific promoters include a rice alpha-amylase (α-Amy) promoter, and a rice glycine rich RNA binding protein (GRRP-A1) promoter.

Exemplary promoters inducible by biotic or abiotic stress (e.g., osmotic stress, drought stress, salt stress, high or low temperatures, hypoxia, anoxia, hydration, pH, chemicals, hormones or a combination thereof) include an *Arabidopsis* rd29A promoter, an *Arabidopsis* corl SA promoter, an *Arabidopsis* kinl promoter, an *Arabidopsis* heat-shock factor (HSF) promoter, an *Arabidopsis* C-repeat-binding factor (CBF1) promoter, an *Arabidopsis* dehydration-responsive element binding protein (DREB1A) promoter, a rice HVA1 promoter, a rice HVA22 promoter, a rice PP2CABA promoter, an alcohol dehydrogenase (Adh) promoter, an ethanol-inducible promoter, an alpha-amylase promoter, and a synthetic ABRC321 promoter.

In some embodiments, the promoter inducible by abiotic stress is a promoter inducible by a plant hormone (e.g., abscisic acid (ABA) or gibberellin (GA)). Exemplary ABA-inducible promoters include the promoter for the rice gene HVA1, the promoter for the rice gene HVA22 and the promoter for the rice PP2CABA gene. An exemplary GA-inducible promoter includes the promoter for alpha-amylase.

In some examples, the promoter described herein may be heterologous to the nucleic acid encoding the PP2CABA in the vector. As used herein, a promoter heterologous to a coding sequence (a gene) refers to a promoter that is not the natural promoter that controls (drives) expression of the gene in native state. For example, the vector of the present disclosure may comprise a promoter derived from a non-PP2CABA gene.

Any of the vectors described herein may be prepared via conventional recombinant technology.

III. Host Cells, Transgenic Plant Cells and Methods of Making Such

Some aspects of the present disclosure feature host cells (e.g., a plant cell or an *Agrobacterium* cell) comprising any of the vectors as described herein. Such host cells (also known as recombinant cells) carry exogenous genetic materials (e.g., the vectors described herein), which can be introduced into the host cell via routine practice. "Exogenous genetic materials" means that the genetic materials are introduced from or produced outside the host cell (or a native plant as described herein). The exogenous genetic material may be derived from a different species as the host cell. In some instances, the exogenous genetic material may be derived from the same species as the host cell and introduced into the host cell such that the resultant recombinant cell comprises extra copies of the genetic material as compared with the wild-type counterpart. The term "transformation" or "transform" as used herein refers to the introduction of exogenous genetic materials into a host cell such as a plant cell. The exogenous genetic materials may be incorporated into the chromosomal DNA of the host cell or remain as extra-chromosomal elements in the host cell.

The host cell may be a plant cell, for example, a cell from a monocotyledonous plant or a dicotyledonous plant (e.g., those described herein).

In certain embodiments, the host cell may be an *Agrobacterium* host cell. An *Agrobacterium* is a soil-borne, Gram-negative, rod-shaped phytopathogenic bacterium which causes crown gall. Exemplary *Agrobacterium* strains include but are not limited to *Agrobacterium tumefaciens* and *Agrobacterium rhizogenes*. *Agrobacterium tumefaciens* infection typically results in crown gall in plants. *Agrobacterium rhizogenes* infection typically results in hairy root disease in plants.

Any suitable conventional method can be used to make the recombinant cells described herein. The acquired genes may be incorporated into chromosomal DNA or introduced as extra-chromosomal elements. The recombinant cells may express the PP2CABA protein stably (e.g., its gene and the operably linked promoter is incorporated into the host cell chromosome). Alternatively, the recombinant cells may express the PP2CABA protein in a transient manner (e.g., its gene and the operably linked promoter remain extra-chromosomal).

Expression constructs include plasmids and viral vectors. A variety of plant viruses that can be employed as vectors are known in the art and include cauliflower mosaic virus (CaMV), geminivirus, brome mosaic virus, and tobacco mosaic virus.

A nucleic acid construct may be introduced directly into a plant cell using techniques ranging from electroporation, PEG poration, particle bombardment, silicon fiber delivery, micro injection of plant cell protoplasts or embryogenic callus or other plant tissue, or *Agrobacterium*-mediated transformation [Hiei et al, Plant J. 6:271-282 (1994)]. Because transformation efficiencies are variable, internal standards (e.g., 35S-Luc) are often used to standardize transformation efficiencies.

Some transient expression methods utilize gene transfer into plant cell protoplasts mediated by electroporation or polyethylene glycol (PEG). These methods require the preparation and culture of plant protoplasts, and involve creating pores in the protoplast through which nucleic acid is transferred into the interior of the protoplast.

Exemplary electroporation techniques are described in Fromm et al, Proc. Natl. Acad. Sci. 82: 5824 (1985). The introduction of DNA constructs using polyethylene glycol precipitation is described in Paszkowski et al, EMBO J. 3: 2717-2722 (1984). PEG-mediated transformation of tobacco protoplasts, which includes the steps of isolation, purification, and transformation of the protoplasts, are described in Lyck et al, (1997) Planta 202: 117-125 and Scharf et al, (1998) Mol CellBiol 18: 2240-2251, and Kirschner et al, (2000) The Plant J 24(3): 397-411. These methods have been used, for example, to identify cis-acting elements in promoters activated by external stimuli, Abel and Theologis (1994) Plant J 5: 421-427; Hattori et al, (1992) Genes Dev 6: 609-618; Sablowski et a/., (1994) £-3OJ 13: 128-137; and Solano et al, (1995) EMBO J 14: 1773-1784), as well as for other gene expression studies (U.S. Pat. No. 6,376,747, hereby incorporated by reference).

PP2CABA expression (e.g., before and after transformation of a vector presented herein in a host cell) may be detected using methods known in the art. For example, real-time polymerase chain reaction may be used to determine PP2CABA mRNA expression. Additional detection methods include an enzyme-linked immunosorbent assay (ELISA) and western blot analysis with an anti-PP2CABA antibody for protein detection.

Plants, as described herein, refer to a plurality of plant cells which are largely differentiated into a structure that is present at any stage of a plant's development. The plant described herein may be a full plant or a part thereof, including a fruit, shoot, stem, root, leaf, seed, panicle, flower petal, or similar structure. The plants may contain a plant tissue, which includes differentiated and undifferentiated tissues of plants including, but not limited to, roots, shoots, leaves, pollen, seeds, tumor tissue and various types of cells in culture (e.g., single cells, protoplasts, embryos, callus, protocorm-like bodies, and other types of cells). Plant tissue may be in planta, in organ culture, tissue culture, or cell culture. Similarly, plant cells may be cells in culture or may be part of a plant. As described above, a plant of the present disclosure may be a monocot or a dicot.

In some embodiments, the plants as described herein are monocotyledonous plants. Monocotyledonous plants are flowering plants having embryos with one cotyledon or seed leaf, parallel leaf veins, and flower parts in multiples of three. Examples of monocots include, but are not limited to maize, wheat, barley, millet, sugarcane, rice, miscanthus, switchgrass and sorghum.

In other embodiments, the plants described herein are dicotyledonous plants. Dicotyledonous plants are flowering plants having embryos with two cotyledons or seed leafs, reticulated leaf veins and flower parts in multiples of fours or fives. Exemplary dicot plants include *Arabidopsis*, soybean, oilseed *Brassica*, peanut, sunflower, safflower, cotton, tobacco, tomato, pea, chickpea, pigeon pea, potato, and cocoa.

The "transgenic plant" described herein refers to a plant that comprises a transgene (such as an exogenous nucleic acid comprising a PP2CABA gene operably linked to a suitable promoter) allowing for expression of a PP2CABA gene in the transgenic plant.

The term transgene as used herein refers to a nucleic acid sequence which is introduced into a plant cell by experimental manipulations. In some embodiments, one or more cells of the transgenic plant carry the transgene. In other embodiments, the genome of the transgenic plant has been altered by the introduction of a transgene.

In some embodiments, the transgenic plants, described herein, over-express PP2CABA protein. As used herein, "expression" of a nucleic acid sequence refers to one or more of the following events: (1) production of an RNA transcript from a DNA sequence (e.g., by transcription); (2) processing of an RNA transcript (e.g., by splicing, editing, 5'cap formation, and/or 3'end processing); (3) translation of an RNA transcript into a polypeptide or protein; and (4) posttranslational modification of a polypeptide or protein.

Over-expression means that the level of the PP2CABA in the transgenic plant is higher than that in the wild-type counterpart. For example, the level of the PP2CABA in the transgenic plant may be at least 20% higher (e.g., 30% higher, 50% higher, 2-fold higher, 5-folder higher, 10-fold higher, 100-folder higher, or above). In some instances, the wild-type parent does not express the PP2CABA protein.

Any of the transgenic plants disclosed herein may exhibit a lower lateral roots (LR) to primary roots (PR) ratio as compared to its wild-type counterpart. For example, the number of lateral roots originating from each primary root may be less in the transgenic plant overexpressing PP2CABA compared to the wild-type plant. In some embodiments, the LR to PR ratio of the transgenic plant overexpressing PP2CABA is at least 1.2 fold, at least 1.5 fold, at least 1.8 fold, at least 2 fold, at least 3 fold, at least 4 fold, at least 5 fold, at least 10 fold, at least 15 fold, at least 20 fold, at least 25 fold, at least 30 fold, at least 40 fold, at least 50 fold, at least 60 fold, at least 80 fold or at least 100 fold lower than its non-transgenic plant counterpart.

Alternatively or in addition, the transgenic plants disclosed herein may exhibit an altered root architecture compared to a wild-type counterpart (e.g., a larger root diameter). In some embodiments, the root diameter of a transgenic plant overexpressing PP2CABA is at least 1%, at least 2%, at least 3%, at least 4%, at least 5%, at least 8%, at least 10%, at least 15%, at least 20%, at least 25%, at least 30%, at least 40%, at least 50%, at least 60%, at least 80%, or at least 100% greater than the root diameter of its wild-type counterpart. In some embodiments, the roots of transgenic PP2CABA-overexpressing plants have increased levels of lignin and/or suberin compared to wild-type counterparts. As described in the Examples below, roots can be cross-sectioned and stained with acriflavine for lignin and fluorol yellow 088 for suberin.

Further, the transgenic plant described herein may have improved stress tolerance (e.g., biotic stress or abiotic stress). Biotic stress can be stress that occurs as a result of damage done to plants by other living organisms, such as bacteria, viruses, fungi, parasites, beneficial and harmful insects, weeds, and cultivated or native plants.

Abiotic stress can be the negative impact of non-living factors on the living organisms in a specific environment. The non-living variable may influence the environment beyond its normal range of variation to adversely affect the population performance or individual physiology of the organism in a significant way. In some embodiments, the abiotic stress is osmotic stress, drought stress, salt stress, or a combination thereof.

In some embodiments, improving the stress tolerance of a plant refers to increasing the ability of a plant to survive under stress, which may be expressed as an increased root length of the plant. In some embodiments, the root length of a transgenic plant that over-expresses PP2CABA protein is at least 5%, at least 10%, at least 15%, at least 20%, at least 25%, at least 30%, at least 40%, at least 50%, at least 60%, at least 80%, or at least 100% greater than its wild-type counterpart. In some embodiments, the root length of a transgenic plant that over-expresses PP2CABA protein is at least 1%, at least 2%, at least 3%, at least 4%, at least 5%, at least 8%, at least 10%, at least 15%, at least 20%, at least 25%, at least 30%, at least 40%, at least 50%, at least 60%, at least 80%, or at least 100% greater than its wild-type counterpart. In other embodiments, the improved growth occurs within 5 days, within 10 days, within 15 days, within 20 days, within 30 days, within 50 days, within 100 days or within 150 days under stress and/or following recovery from stress.

In some embodiments, improving the stress tolerance of a plant may be expressed as increased water holding capability in roots under stress (e.g., drought stress). The water holding capability in roots may be calculated as the water content (%) using the formula (FW−DW)/FW×100, wherein FW is the fresh weight measurement of roots and DW is the dry weight measurement. The dry weight measurement may be determined by drying roots in a 65 degree Celsius oven for 18 hours (see Examples below).

In some embodiments, improving the stress tolerance of a plant may be expressed as an improved morphological appearance of a plant overexpressing PP2CABA protein as compared to wild-type (e.g., less wilted leaves compared to wild-type). For example, a less wilted leaf would be more rigid and straight in appearance than its wild-type counterpart.

In some embodiments, the methods described herein may improve the ability of plants to survive osmotic stress. Osmotic stress may be mimicked by exposure to polyethylene glycol (PEG). In some embodiments osmotic stress is mimicked using 20% PEG6000. In some embodiments, plants may be allowed to recover from osmotic stress (e.g., plants under osmotic stress mimicked using 20% PEG6000 may be grown in hydroponic solution, see Examples below).

In some embodiments, the inventive methods improve the ability of plants to survive drought stress. Drought stress may be mimicked by dehydration (see Examples below). In some embodiments, recovery from drought stress may be achieved through rehydration.

The vectors constructed may be introduced into the plant host system using procedures known in the art (reviewed in WO 01/29242 and WO 01/31045). As described above, one or more plant cells in a plant may be modified using methods known in the art.

Techniques for transforming a wide variety of higher plant species for transient expression of an expression cassette are well known [see, for example, Weising et al, Ann. Rev. Genet. 22:421-477(1988)]. Variables of different systems include type nucleic acid transferred (DNA, RNA, plasmid, viral), type of tissue transformed, means of introducing transgene(s), and conditions of transformation. Plant tissues suitable for transient expression include cultured cells, either intact or as protoplasts (in which the cell wall is removed), cultured tissue, cultured plants, and plant tissue such as leaves.

As an example, for plant cells, a method for transferring DNA into a host organism is inoculation or infiltration of plant cells (from in vitro culture), of explants (like hypocotyls, roots) or of organs (like leaves or flowers) with *Agrobacterium tumefaciens* or *Agrobacterium rhizogenes*. Another method is the direct introduction of DNA (like electroporation or PEG mediated transfection) into plant protoplasts.

Nucleic acids can also be introduced into plants by direct injection. Transient gene expression can be obtained by injection of the DNA into reproductive organs of a plant (see, for example, Pena et al., (1987) Nature, 325.:274), such as by direct DNA transfer into pollen (see, for example, Zhou et al., (1983) Methods in Enzymology, 101:433; D. Hess (1987) Intern Rev. Cytol., 107:367; Luo et al., (1988) Plant Mol. Biol. Reporter, 6:165. DNA can also be injected directly into the cells of immature embryos (see, for example, Neuhaus et al., (1987) Theor. Appl. Genet: 75:30; and Benbrook et al., (1986) in Proceedings Bio Expo 1986, Butterworth, Stoneham, Mass., pp. 27 54), (1996) Nat. Biotech. 14:745-750).

*Agrobacterium*-mediated transformation is applicable to both dicots and monocots. Optimized methods and vectors for *Agrobacterium*-mediated transformation of plants in the family Graminae, such as rice and maize have been described (see, for example, Heath et al., (1997) Mol. Plant-Microbe Interact. 10:221-227; Hiei et al., (1994) Plant J. 6:271-282 and Ishida et al., (1996) Nat. Biotech. 14:745-750).

Another useful basic transformation protocol involves a combination of wounding by particle bombardment, followed by use of *Agrobacterium* for DNA delivery (see, for example, Bidney et al., (1992) Plant Mol. Biol. 18:301-313). Both intact meristem transformation and a split meristem transformation methods are also known (U.S. Pat. No. 6,300,545, hereby incorporated by reference).

Additional methods utilizing Agrobacteria include agroinfection and agroinfiltration. By inserting a viral genome into the transfer DNA (T-DNA), *Agrobacterium* can be used to mediate the viral infection of plants (see, for example, U.S. Pat. No. 6,300,545, hereby incorporated by reference). Following transfer of the T-DNA to the plant cell, excision of the viral genome from the T-DNA (mobilization) is required for successful viral infection. This *Agrobacterium*-mediated method for introducing a virus into a plant host is known as agroinfection (see, for example, Grimsley, "Agroinfection" pp. 325-342, in Methods in Molecular Biology, vol 44: *Agrobacterium* Protocols, ed. Gartland and Davey, Humana Press, Inc., Totowa, N. J.; and Grimsley (1990) Physiol. Plant. 79:147-153).

Ballistic transformation techniques are described in Klein et al, (1987) Nature 327: 70-73. Biolistic transient transformation is used with suspension cells or plant organs. For example, it has been developed for use in Nicotiana tabacum leaves, Godon et al (1993) Biochimie 75(7): 591-595. It has also been used in investigating plant promoters, (Baum et al, (1997) Plant J 12: 463-469; Sfromvik et al, (1999) Plant Mol Biol 41(2): 217-31, Tuerck and Fromm (1994) Plant Cell 6: 1655-1663; and U.S. Pat. No. 5,847,102, hereby incorporated by reference), and to characterize transcription factors (Goff et al, (1990) EMBOJ9: 2517-2522; Gubler et al, (1999) Plant J 17: 1-9; and Sainz et al, (1997) Plant Cell 9: 611-625).

In a specific embodiment, once the presence of a PP2CABA gene of interest and one or more enhanced features (e.g., exhibits a lower lateral roots (LR) to primary roots (PR) ratio, a larger root diameter, a higher tolerance to abiotic stress, increased levels of lignin and/or suberin, or a combination thereof, as compared with a non-transgenic plant counterpart growing under the same conditions) are ascertained, a plant may be regenerated using procedures known in the art. Transgenic plants that stably over-express a PP2ABA gene as described herein may be selected by examining genome insertion of a transgene described herein following conventional technology. As described above, the presence of enhanced features may also be ascertained using methods known in the art.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Transgenic Plant Expressing Exogenous PP2CABA

Materials and Methods
Plant Materials

The japonica rice (*Oryza sativa* cv Tainung 67) was used in this study. Plasmids were introduced into *Agrobacterium tumefaciens* strain EHA105, and rice transformation was performed as described (Chen et al., J Biol Chem, 277: 13641 (2002)). The PP2CABA mutant seeds were obtained from the Taiwan Rice Insertional Mutant (TRIM) library (Hsing et al., Plant Molecular Biology, 63:351 (2007)). For hydroponic culture of rice seedlings, seeds were sterilized with 3% NaOCl for 30 minutes, washed extensively with distilled water, and germinated in petri dishes with wetted filter papers at 37° C. in the dark. After 48 h of incubation, germinated seeds were cultivated in Yoshida solution (Yoshida et al., International Rice Research Institute, 3 (1976)). The culture solution was replaced with fresh solution every 2 days. For observation of root growth in glass tube with phytagel, sterilized rice seeds were germinated on the surface of plate with Yoshida solution with 0.3% phytagel without sugar in the dark at 28° C. for about 48 hours. The germinated seedlings were then transplanted to glass tubes, which were 22 cm in height and 4.5 cm in diameter, and each filled with 150 ml Yoshida solution with 0.3% phytagel without sugar. 6 cm plastic dish was used to cover the glass tube and sealed by micropore tape to allow light penetration and gas exchange and prevent the medium from becoming contaminated by external microbes. Seedlings were grown under a 14-h-light/10-h-dark cycle in a 28° C. chamber.

Phylogenetic Analysis

The PP2CABA homologs were identified by BLAST search of the National Center for Biotechnology Information database (world wide web (www) link: blast.st-va.ncbi.nlm.nih.gov/) with the full-length PP2CABA. Deduced amino acid sequences of PP2CABA homologs were aligned with the AlignX (Vector NTI, version 9.0.1; Invitrogen) programs. The unrooted phylogenetic tree was constructed using the MEGA6 phylogenetic analysis program. Evolutionary relationships were deduced using the neighbor-joining algorithm.

RT-PCR and Real-Time Quantitative RT-PCR Analyses

Total RNA was purified from rice tissues using Trizol reagent (Invitrogen) and treated with RNase-free DNase I (Promega). The DNase-digested RNA sample was used for reverse transcription by Superscript III reverse transcriptase (Invitrogen). Samples, which served as cDNA stocks for PCR analysis, were stored at −70° C. RT-PCR analysis was performed in a 50-μl solution containing 5-μl cDNA stock using Taq DNA polymerase (Viogene). RT-PCR products were fractionated in a 1.5% agarose gel and visualized by ethidium bromide staining. All RT-PCR analyses were performed from at least two batches of RNA samples with similar results. For quantitative RT-PCR analyses, 5-μl of cDNA was mixed with primers and the 2× Power SYBR Green PCR Master Mix reagent (Roche) and applied to an ABI 7500 Real-Time PCR system (Applied Biosystems). The quantitative variation between different samples was evaluated by the Δ-Δ cycle threshold method, and the amplification of ubiquitin 5 was used as an internal control to normalize all data.

Plasmid Construction

The PP2CABA cDNA was amplified by RT-PCR from RNA collected from dry embryos isolated from mature rice seeds. The specific primers used to isolate PP2CABA cDNA were designed based on the full-length cDNA sequence annotated with the Rice Genome Annotation Project database (world wide web (www) link: rice.plantbiology.msu.edu/). The full-length PP2CABA cDNA (1287 bp) was synthesized by RT-PCR and ligated into the pGEM-T Easy cloning vector (Promega), generating pTA-PP2CABA. For mutation of the DGH catalytic motif of PP2CABA, a back-to-back PCR-based oligonucleotide-directed mutagenesis approach (Hemsley et al., Nucleic Acids Res, 17:6545 (1989)) was used to generate pTA-PP2CABA (D100A).

For the construction of bacteria expression plasmids, the abi2 cDNA was amplified by RT-PCR from RNA collected from 10-days-old *Arabidopsis* seedlings and subcloned into the pET-41a expression vector (Novagen), generating pGST-ABI2 as positive control. PP2CABA and PP2CABA (D100A) coding sequence was PCR amplified from pTA-PP2CABA and pTA-PP2CABA (D100A), and subcloned into the pET-41a expression vector, generating pGST-PP2CABA and pGST-PP2CABA (D100A).

For the expression pattern analysis, since PP2CABA have a neighbor gene (LOC_Os06g48310) 736 bp upstream from the translation start site, the 708 bp PP2CABA promoter sequence was isolated by genomic PCR. The CaMV35S promoter upstream of GUS in pCAMBIA1301 was replaced with the PP2CABA promoter, generating pPP2CABA-GUS.

For subcellular localization analysis, The NOS terminator was excised from pAHC18 (Lu et al., Plant Cell, 19:2484 (2007)) and subcloned into pBluescript KS+ (Stratagene), generating pBS-NOS. The CaMV35S promoter was PCR amplified from pCAMBIA-1301 and subcloned into the pBS-NOS, generating p35S-NOS. The GFP coding sequence was PCR amplified from pCAMBIA-1302 and inserted between the CaMV35S promoter and NOS terminator in p35S-NOS, generating p35S-GFP. The coding sequence of PP2CABA was fuse to GFP coding sequence and subcloned into the p35S-NOS, generating p35S-PP2CABA-GFP. For enhance the GFP signal in vacuole, F64L/S65T double mutation (Stauber et al., Biotechniques, 24:462 (1998)) was introduced into the GFP coding sequence by back-to-back PCR approach, generating p35S-GFP6 and p35S-PP2CABA-GFP6. For mutation of the second ATG in PP2CABA coding sequence and for remove the coding sequence before second ATG in PP2CABA, back-to-back PCR were performed to generate p35S-PP2CABA (M41A)-GFP and p35S-PP2CABA (41-327)-GFP. The PP2CABA promoter was fuse to PP2CABA-GFP6 coding sequence and subcloned into the multiple cloning sites of binary vector pCAMBIA-1301, generating pPP2CABA-PP2CABA-GFP6.

For molecular weight analysis, a duplicated HA epitope was add to C terminal of PP2CABA coding sequence by PCR. The GFP coding sequence in p35S-GFP was replaced with the double HA-tagged PP2CABA coding sequence, generating p35S-PP2CABA-dHA. For mutation of the second ATG in PP2CABA coding sequence and for remove the coding sequence before second ATG in PP2CABA, back-to-back PCR were performed to generate p35S-PP2CABA (M41A)-dHA and p35S-PP2CABA (41-327)-dHA.

For inducible overexpression in stable transgenic plants, the XVE coding sequence and E9 terminator from pER8 (Zuo et al., Plant J, 24:265 (2000)) was fused to rice Actin 1 promoter from pAct-LN (Chen et al., J Biol Chem, 277:13641 (2002)) and subcloned into the pBluescript KS+, generating pAct1-XVE-E9T. The CaMV35S promoter upstream of PP2CABA in p35S-PP2CABA-dHA and p35S-PP2CABA (D100A)-dHA were replaced with the LexA promoter from pER8, generating pLexA-PP2CABA-dHA and pLexA-PP2CABA (D100)-dHA. Both of ActI-XVE-E9T and LexA-PP2CABA-dHA cassettes were subcloned into the multiple cloning sites of binary vector pCAMBIA-1301, generating pXVE-PP2CABA-dHA and pXVE-PP2CABA (D100A)-dHA.

Expression and Phosphatase Activity Assay of GST Fusion Proteins

GST fusion proteins were overexpressed in *E. coli* BL21 (DE3) pLysS and purified on glutathione sepharose 4B beads (Amersham Biosciences) according to the manufacturer's protocols. Phosphatase activity assays were performed according to the manufacturer's instructions using a non-radioactive serine/threonine phosphatase assay system (Promega).

Subcellular Localization Analysis of GFP Fusion Protein

For detection of PP2CABA-GFP in protoplasts, the released protoplast cells from leaf sheath of 10-day-old rice seedlings grow in MS medium were isolated and transformed via the polyethylene glycol (PEG 4000) method (Zhang et al., Plant Methods, 7:30 (2011)). Protoplast cells expressing GFP were imaged with a Zeiss LSM510 confocal microscope using a 488 nm laser line for excitation and a 505 nm to 530 nm band pass filter for emission.

Antibodies and Immunoblot Analysis

The anti-PP2CABA polyclonal antibodies were produced against synthetic peptides (N-QENHLPERPTNDQAS-C, amino acid residues 313 to 327) derived from C terminal region of PP2CABA. Polyclonal anti-PP2CABA antibodies were raised in rabbits and purified by immobilized peptide affinity chromatography (GenScript). Mouse monoclonal antibody against HA tag was purchased from Sigma-Aldrich. The immunoblot analysis with the anti-PP2CABA primary antibody diluted at 1:2000 was performed as described (Lu et al., Plant Cell, 19:2484 (2007)). Horseradish peroxidase-conjugated antibody against rabbit immunoglobulin G (Amersham Biosciences) was used as a secondary antibody. Protein signals were detected by chemiluminescence with ECL (Amersham Bioscience). Ponceau S staining of proteins was used for a loading control.

Microarray Analysis

Total RNA was extracted from roots of rice seedlings using the Qiagen RNeasy Plant Mini Kit (Qiagen) according to the manufacturer's instructions. RNA quality was examined by the Agilent 2100 bioanalyzer (Agilent Technologies), and biotinylated target RNA was prepared from total RNA. Samples were hybridized to the Affymetrix Rice GeneChip as described in the GeneChip Expression Analysis Technical Manual. The hybridization signals were scanned with an Affymetrix GeneChip scanner 3000 7G, and the cell intensity (CEL) files were obtained from Affymetrix GCOS version 1.4 software. CEL files were loaded into GeneSpring GX 11.0 (Agilent Technologies). Filtering tools in the GeneSpring software were used to identify genes significantly up-regulated and down-regulated between different chips.

GUS Assay

Tissues were placed in GUS assay buffer containing (0.1 M NaPO4 buffer pH 7.0, 10 mM EDTA, 0.1% Triton X-100, 0.5 mM potassium ferricyanide pH 7.0, and 1.0 mM X-glucuronide) and incubated overnight at 37° C. Vacuum aspiration was applied during initial 30 minutes. After GUS staining, leaves were incubated in 70% ethanol at 65° C. for 1 hour to remove chlorophyll.

Histochemical Staining of Cell Wall

Methonal fixed roots were embedded in 5% agar and cut into 100 μm cross sections using a vibratome (DOSAKA DTK-1000). To check for autofluorescence, sections were viewed under a Zeiss Axiolmager Z1 fluorescence microscope with UV illumination using excitation filter G 365, chromatic beam splitter FT 395, and barrier filter LP 420. To check for lignin distribution, sections were stained with Acriflavine as described (Rocha et al., Front Plant Sci, 5:102 (2014)). Sections were imaged with a Zeiss LSM 510 META confocal microscope using a 488 nm laser line for excitation and a 505 to 550 nm band pass filter for emission. To check for suberin lamellae, sections were stained with Fluorol Yellow 088 as described (Brundrett et al., Biotech Histochem, 66:111 (1991); Landgraf et al., Plant Cell, 26:3403 (2014)). Sections were imaged with a Zeiss LSM 780 confocal microscope using an excitation wavelength of 405 nm for autofluorescence and 488 nm for fluorol yellow 088. The emission filter settings were 418 nm to 480 nm for autofluorescence and 524 nm to 594 nm for fluorol yellow 088.

Stress Testing

For osmotic stress tolerance analysis, ten-day-old seedlings cultured in the Yoshida solution in growth chamber were used. Seedlings were transferred to culture solution containing 20% PEG6000 to allow the development of osmotic stress. After all the leaves are wilted, seedlings were recovered by Yoshida solution. For drought stress tolerance analysis, 16-day-old seedlings cultivated in pots containing vermiculite with Yoshida solution in growth chamber were used. Yoshida solution was removed to allow drought stress development. After dehydration for 15-days, seedlings were recovered by Yoshida solution.

Primers

Nucleotides for all primers used for PCR and RT-PCR analyses are provided in Table 1.

TABLE 1

Primers used for plasmid construction, genotyping, RT-PCR and Q-PCR

| Primer | Sequence | Use |
|---|---|---|
| 2C1 | 5'-GATGGAGAGACCGTTGGACTGTTTG-3' (SEQ ID NO: 5) | pp2caba genotyping, RT-PCR and Q-PCR |
| 2C2 | 5'-GATTGAGGACCAACACTTAACCTGC-3' (SEQ ID NO: 6) | pp2caba RT-PCR |
| 2C3 | 5'-GAACATTCATGATACAGACCAGGAC-3' (SEQ ID NO: 7) | pp2caba genotyping |
| 2CE4R | 5'-CCTGCATCTCGATTGTGGCTGGTTT-3' (SEQ ID NO: 8) | pp2caba Q-PCR |
| GUS2 | 5'-ACCAACGCTGATCAATTCCACAG-3' (SEQ ID NO: 9) | T-DNA genotyping |
| RBSP | 5'-ACTGATAGTTTAAACTGAAGGCGG-3' (SEQ ID NO: 10) | T-DNA genotyping |

TABLE 1-continued

Primers used for plasmid construction, genotyping, RT-PCR and Q-PCR

| Primer | Sequence | Use |
|---|---|---|
| HPA1F | 5'-CAAGCTTTCCGACTTCTGAGTCGGTGGCGAGTAC-3' (SEQ ID NO: 11) | pPP2CAGA-GUS |
| SBPA1R2 | 5'-CACTAGTCAGATCTACCATGCACGCGAACGACGGAGGAGG-3' (SEQ ID NO: 12) | pPP2CAGA-GUS |
| SA1F | 5'-GCGACTAGTCTCTCGCAGGGAGCGGA-3' (SEQ ID NO: 13) | pGST-PP2CABA |
| HA1R | 5'-GCGAAGCTTTTAGGAGGCTTGATCATTCGTCGGTC-3' (SEQ ID NO: 14) | pGST-PP2CABA |
| SABI2F | 5'-GCGACTAGTGACGAAGTTTCTCCTGCAGTCGCTGTTCC-3' (SEQ ID NO: 15) | pGST-ABI2 |
| HABI2R | 5'-GCGAAGCTTTCAATTCAAGGATTTGCTCTTGAATTTCC-3' (SEQ ID NO: 16) | pGST-ABI2 |
| M3F | 5'-GCTGGTCATGGTGGAGCTCGAGCAGCAGAATTCGTC-3' (SEQ ID NO: 17) | PP2CABA (D100A) |
| M1R | 5'-AAAGACACCAAACAGTCCAACGGTCTCTCCATC-3' (SEQ ID NO: 18) | PP2CABA (D100A) |
| NA1F | 5'-CGCGGCCGCACCATGCGTGAGGTGCTCCTCCTCG-3' (SEQ ID NO: 19) | PP2CABA-dHA |
| SA1-dHAR | 5'-CGCACTAGTTCAAGCGTAGTCTGGAACGTCGTATGGGTAACCAGCGTAGTCTGGAACGTCGTATGGGTAAGGGGAGGCTTGATCATTCGTCG-3' (SEQ ID NO: 20) | PP2CABA-dHA |
| M41AF | 5'-GCTGGGCTCGCCGGAGAGG-3' (SEQ ID NO: 21) | PP2CABA (M41A) |
| M41AR | 5'-CAAGCGCACCTCGCCGTCGT-3' (SEQ ID NO: 22) | PP2CABA (M41A) |
| A1-41F | 5'-ATGGGGCTCGCCGGAGAGG-3' (SEQ ID NO: 23) | PP2CABA (41-327) |
| P35SR | 5'-GGTGCGGCCGCGTCAAGAGTCCCCCGTGTTC-3' (SEQ ID NO: 24) | PP2CABA (41-327) |
| MGFP6F | 5'-CTCACCTATGGTGTTCAATGCTTTTCAA-3' (SEQ ID NO: 25) | GFP6 |
| MGFP6R | 5'-AGTAGTGACAAGTGTTGGCCACGGAA-3' (SEQ ID NO: 26) | GFP6 |
| MPACT1F | 5'-CGCCAATTGGTCATTCATATGCTTGAGAAGAGAGTCG-3' (SEQ ID NO: 27) | Actin 1 promoter |
| KPACT1R | 5'-CGCGGTACCCTTCTACCTACAAAAAAGCTCCGCACG-3' (SEQ ID NO: 28) | Actin 1 promoter |
| KXVEF | 5'-CGCGGTACCATGAAAGCGTTAACGGCCAGGC-3' (SEQ ID NO: 29) | XVE cds-E9 terminator |
| SXVER | 5'-CGCACTAGTGTTTGGGATGTTTTACTCCTCATATTA-3' (SEQ ID NO: 30) | XVE cds-E9 terminator |
| XPLEXAF | 5'-CGCTCTAGACAGCTTGGGCTGCAGGTCGAGGC-3' (SEQ ID NO: 31) | Lex A promoter |
| NPLEXAR | 5'-CGCGCGGCCGCCTCGAGGCTAGAGTCGACTAGCTTCAG-3' (SEQ ID NO: 32) | Lex A promoter |
| Os06g04090 F | 5'-CAAGAGGTGACGATGGAGATGA-3' (SEQ ID NO: 33) | SWN1 Q-PCR |
| Os06g04090 R | 5'-CGTAGACCGACCAGATTAAGAGTAGA-3' (SEQ ID NO: 34) | SWN1 Q-PCR |
| Os08g02300 F | 5'-TGGCACTGTAACACATGATTCG-3' (SEQ ID NO: 35) | SWN2 Q-PCR |
| Os08g02300 R | 5'-TCTTCTTACTTGTCTTGTCTCTGTAATTACTG-3' (SEQ ID NO: 36) | SWN2 Q-PCR |
| Os08g33940 F | 5'-AAAAAGGAAAAAAAAATGAGGGGACA-3' (SEQ ID NO: 37) | MYB96 Q-PCR |
| Os08g33940 R | 5'-CACCAGCTTTGTGCTTTTGATGATCTA-3' (SEQ ID NO: 38) | MYB96 Q-PCR |
| Os02g56700 F | 5'-CCAAAGATAATAAAAGCAGAGACATGA-3' (SEQ ID NO: 39) | CCR10 Q-PCR |
| Os02g56700 R | 5'-TAAGCCGCCGCCAAAAT-3' (SEQ ID NO: 40) | CCR10 Q-PCR |
| Os01g34560 F | 5'-CGTCCAGCTCCCCGAAAT-3' (SEQ ID NO: 41) | KCS Q-PCR |
| Os01g34560 R | 5'-TAGGGTCGTTGTACGTCGTTTATC-3' (SEQ ID NO: 42) | KCS Q-PCR |
| Os03g08360 F | 5'-TGCGATGCCGGTTAAGGT-3' (SEQ ID NO: 43) | KCS Q-PCR |
| Os03g08360 R | 5'-TGGCTCATAAACCGACTTGCTAA-3' (SEQ ID NO: 44) | KCS Q-PCR |
| Os10g36100 F | 5'-ACAGCACCAACGCACGCAAGATGAT-3' (SEQ ID NO: 45) | LTP Q-PCR |
| Os10g36100 R | 5'-GTGAACGGCGGCGACGGAGC-3' (SEQ ID NO: 46) | LTP Q-PCR |

TABLE 1-continued

Primers used for plasmid construction, genotyping, RT-PCR and Q-PCR

| Primer | Sequence | Use |
|---|---|---|
| Os11g10460 F | 5'-CGAGGTCAGGAAAGTCTGCTCCAAG-3' (SEQ ID NO: 47) | POX Q-PCR |
| Os11g10460 R | 5'-CTGTCCCAGCAAGATGCACATGAAC-3' (SEQ ID NO: 48) | POX Q-PCR |
| Os12g02080 F | 5'-TCCAGTAGTGCAAACGCACATT-3' (SEQ ID NO: 49) | POX Q-PCR |
| Os12g02080 R | 5'-AAGAAATTAAGGGAGATGTTGCAAAC-3' (SEQ ID NO: 50) | POX Q-PCR |
| LEA3 F | 5'-GCCGTGAATGATTTCCCTTTG-3' (SEQ ID NO: 51) | LEA3 Q-PCR |
| LEA3 R | 5'-CACACCCGTCAGAAATCCTCC-3' (SEQ ID NO: 52) | LEAE Q-PCR |

Underlined areas indicate restriction sites: AAGCTT, HindIII site; ACTAGT, SpeI site; AGATCT, BglII site; GCGGCCGC, NotI site; CAATTG, MfeI site; GGTACC, KpnI site; TCTAGA, XbaI site.

Accession Numbers

Sequence data from this article can be found in the Rice Genome Annotation Project database (rice.plantbiology.msu.edu) or in the NCBI database under the following accession numbers: PP2CABA/OsPP91 (LOC 0s06g48300); OsSWN1 (LOC_Os06g04090); OsSWN2 (LOC_Os08g02300); rice AtMYB96-like gene (LOC_Os08g33940); Cinnamoyl-CoA reductase gene (LOC_Os02g56700); 3-ketoacyl-CoA synthase genes (LOC_Os01g34560 and LOC_Os03g08360); lipid transfer protein gene (LOC_Os10g36100); class III peroxidase genes (LOC_Os11g10460 and LOC_Os12g02080); LEA3 gene (LOC_Os05g46480); ubiquitin 5 gene (AK061988); PP2CABA-like proteins from *Hordeum vulgare* (BAJ97055), *Triticum aestivum* (ABS11093), *Brachypodium distachyon* (XP_003563487), *Setaria italica* (XP_004966135), *Zea mays* (ACF86324), *Sorghum bicolor* (XP_002448686), *Mesembryanthemum crystallinum* (BAB88944), *Populus trichocarpa* (XP_002308720), *Physcomitrella patens* (XP_001755313) and *Selaginella moellendorffii* (XP_002969991); OsPP18 (LOC_Os02g05630); OsPP70 (LOC_Os04g56450); OsPP86 (LOC_Os06g33530); OsPP87 (LOC_Os06g33549); OsPP22/DCW11 (LOC_Os02g15594); OsPP11 (LOC_Os01g43100); OsPP80 (LOC_Os05g50970); AtPP2C69 (At5g10740); AtPP2C71 (At5g24940); AtPP2C59/WIN2 (At4g31750); AtPP2C11 (At1g43900); AtPP2C76 (At5g53140).

Results

Identification of PP2CABA

Figure 2:
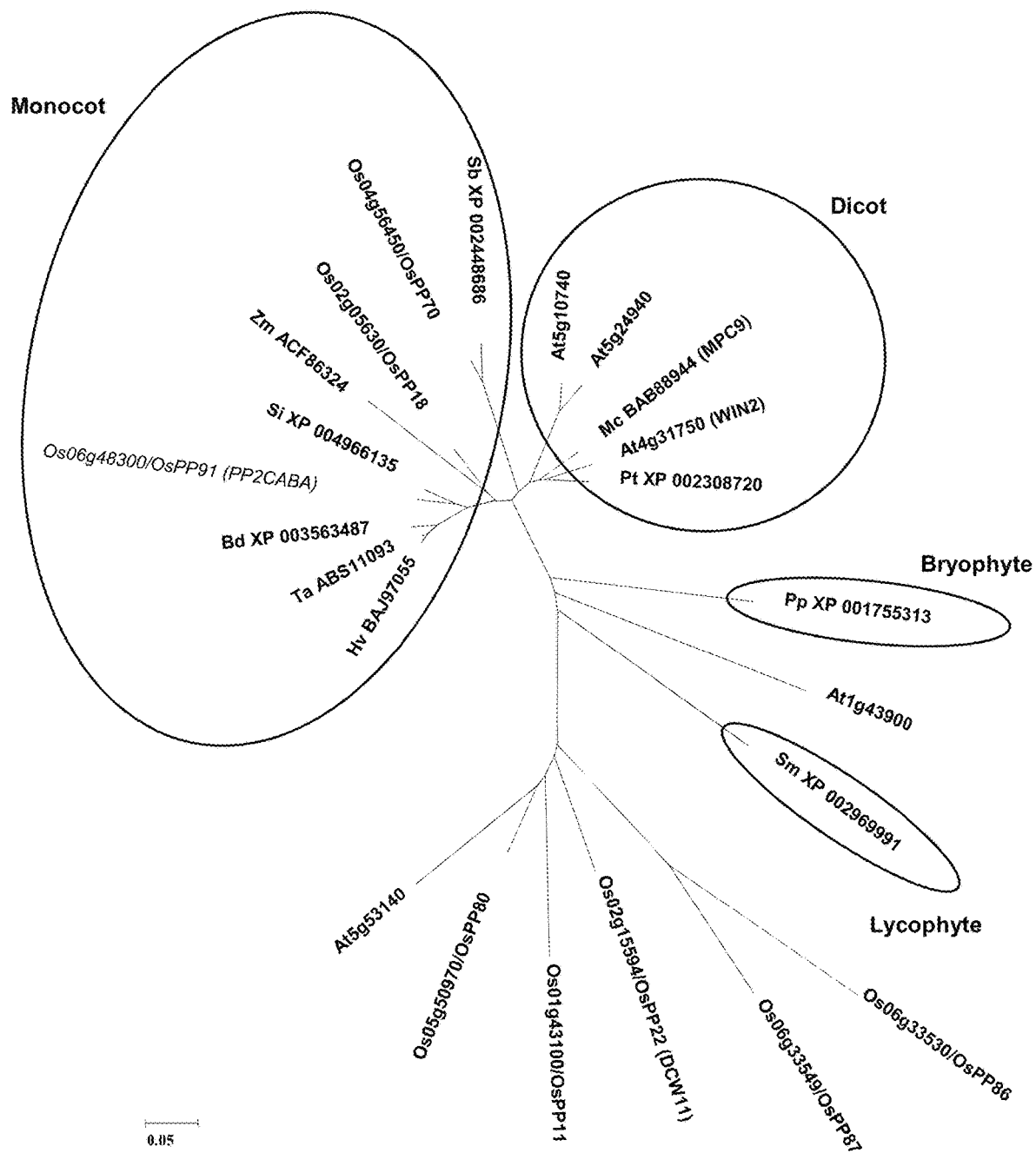
FIG. 2 is a diagram showing phylogenetic analysis based on the comparison of PP2CABA homologs in land plants. Amino acid sequences of 23 PP2CABA from twelve plant species were analyzed using the neighbor-joining method. The scale value of 0.05 indicates 0.05 amino acid substitutions per site. Plant species: At, *Arabidopsis thaliana*; Bd, *Brachypodium distachyon*; Hv, *Hordeum vulgare*; Mc, *Mesembryanthemum crystallinum*; Os, *Oryza sativa*; Pp, *Physcomitrella patens*; Pt, *Populus trichocarpa*; Sm, *Selaginella moellendorffii*; Si, *Setaria italic*; Sb, *Sorghum bicolor*; Ta, *Triticum aestivum*; Zm, *Zea mays*.
Figure 3A:
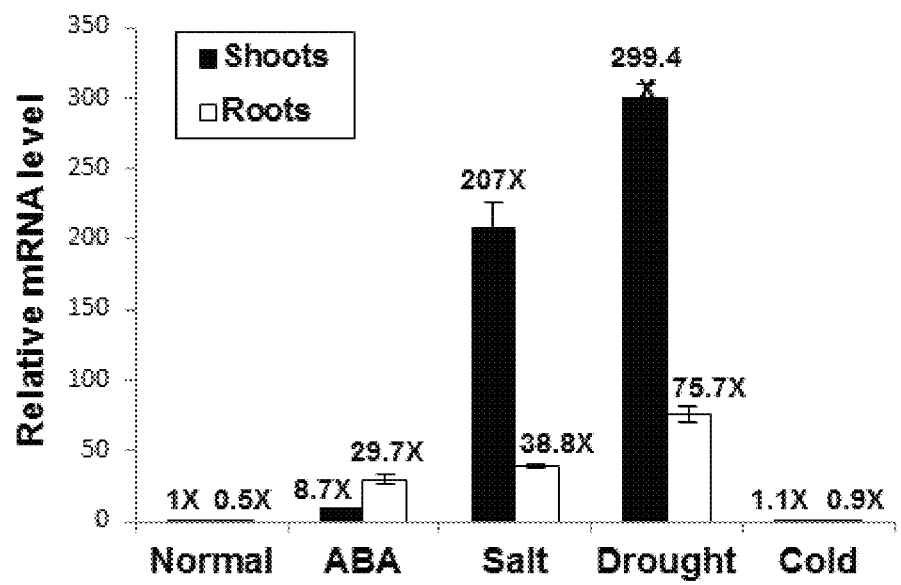
FIG. 3A to FIG. 3D include diagrams showing plants have higher PP2CABA expression under induction by ABA and abiotic stress and are expressed in meristematic tissues.
Figure 3B:
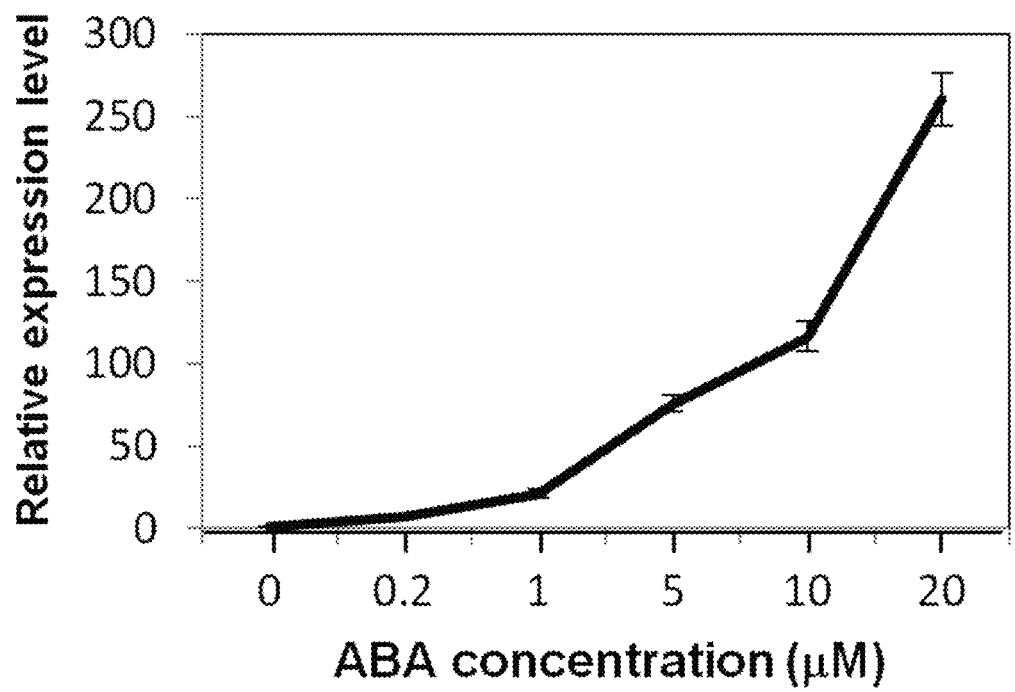
Figure 3C:
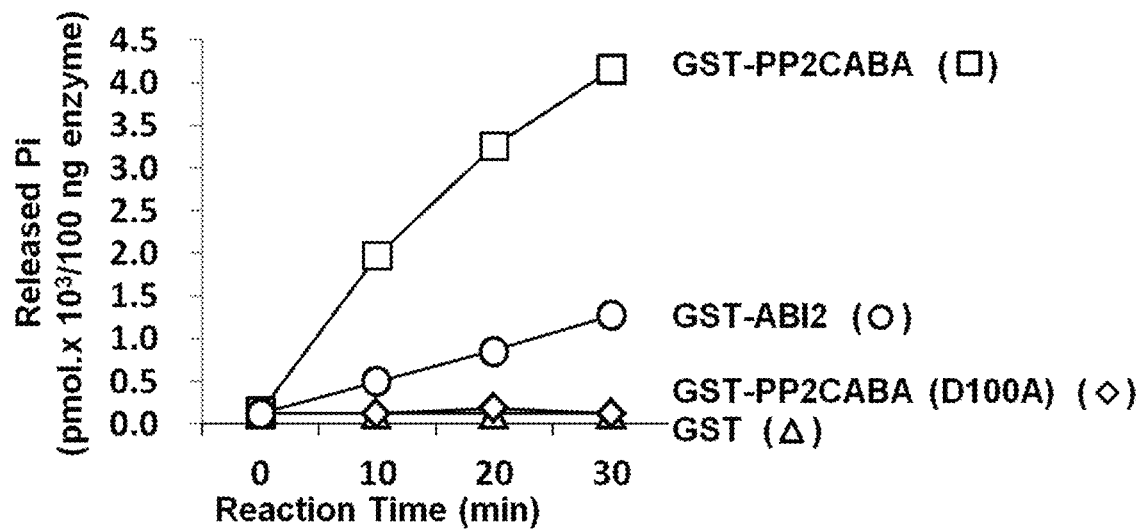
Figure 3D:
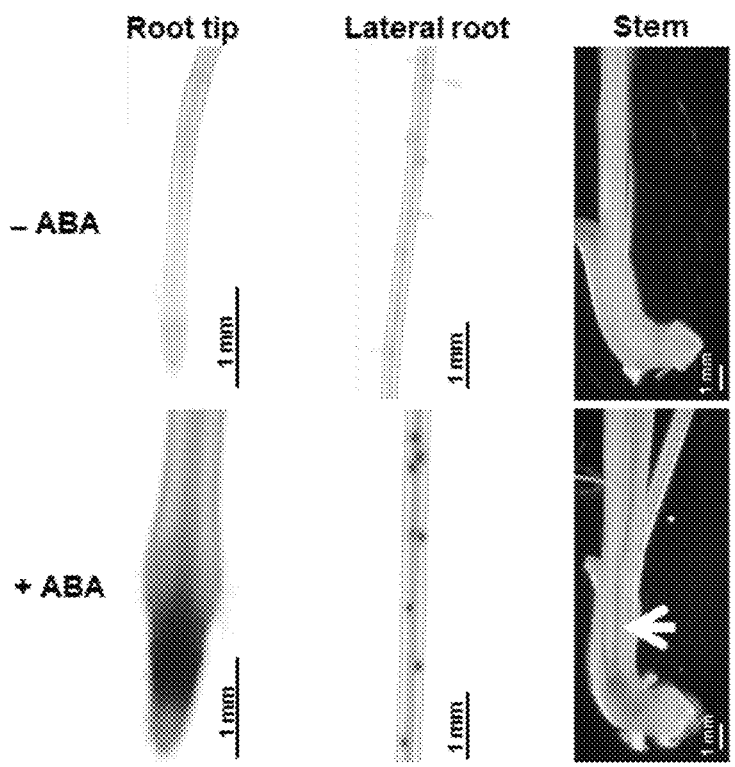

To identify novel signaling factors that regulate stress responses in rice, a transcriptomics analysis was performed for rice seedlings treated with ABA. Among 90 PP2C genes present in the rice genome (Singh et al., BMC Genomics, 11:435 (2010)) (FIG. 1), it was found that PP2CABA/OsPP91 (LOC_Os06g48300) is highly induced by ABA, and phylogenetic analysis shows that it belongs to the clade-F2 PP2C subfamily with unknown function. PP2CABA homologs are present in genomes of various land plant species, ranging from bryophyte to angiosperms (FIG. 2). The expression of PP2CABA is also up-regulated by salt and drought in shoots and roots of rice seedlings (FIG. 3A). The expression of PP2CABA in roots was induced by 0.2 µM ABA, and increased with ABA concentrations in a dose-dependent manner (FIG. 3B). GST-PP2CABA fusion protein expressed and purified from *E. coli* exhibited phosphatase activity in contrast to an inactive form of GST-PP2CABA, GST-PP2CABA(D100A), in which the Asp residue within the catalytic cleft was replaced with Ala (Himmelbach et al., EMBO J, 21:3029 (2002)) (FIG. 3C). GUS staining analysis of transgenic rice carrying construct PP2CABA: GUS revealed that the PP2CABA promoter was inactive normally but induced by ABA in basal meristem region in root tips, LR primordia and young leaves (FIG. 3D).

The nucleotide sequence of PP2CABA (long form, L) is shown below:

SEQ ID NO: 1
ATGCGTGAGGTGCTCCTCCTCGGCTCGTTGGTGGTTCTCGCCTTGTTGTC

GCTGTTCCCGTGCTGCTCCTGTCTCTCGCAGGGAGCGGAGGAGGAGGAGG

ACGACGGCGAGGTGCGCTTGATGGGGCTCGCCGGAGAGGCCGCTGGCTCG

CCTGGCAGTGGCGGCGGGTTCAGTGCAAATGGTAAATTTAGCTATGGTTA

TGCGAGCTCTCCTGGAAAAAGATCCTCCATGGAGGACTTCTATGACACCA

GAATTGATGGTGTCGATGGAGAGACCGTTGGACTGTTTGGTGTCTTTGAT

GGTCATGGTGGAGCTCGAGCAGCAGAATTCGTCAAGCAGAACCTCTTCAC

CAATTTAATCAAGCACCCAAAGTTATTCAGTGATACCAAGTCTGCAATTG

CTGAAACTTACACTAGCACGGACTCTGAACTTCTGAAAGCTGAAACCAGC

CACAATCGAGATGCAGGGTCGACTGCCTCCACTGCAATTCTCGTAGGCGA

CCGTCTGCTCGTTGCAAATGTTGGAGATTCTAGGGCTGTCATTTGTAGAG

GAGGAGATGCTATAGCTGTGTCAAGAGACCACAAGCCTGATCAGTCAGAC

GAGAGGCAGAGGATAGAGGATGCTGGTGGTTTTGTGATGTGGGCTGGAAC

ATGGCGCGTGGGTGGTGTTCTTGCTGTCTCTCGAGCATTTGGTGACAAAC

TCCTGAAGCAATATGTGGTTGCTGATCCAGAGATCAAGGAGGAGGTGGTC

GACAGCTCTCTCGAGTTCCTCATCCTTGCTAGTGATGGCCTCTGGGACGT

GGTGACCAACGAGGAAGCTGTGGCCATGGTGAAGCCAATTCTGGATTCAG

AGCAGGCTGCAAAGAAGCTCCTCCAGGAGGCCTCACAGAGGGGAAGCGCA

GACAACATCACCTGCCTCGTCGTCCGTTTCTTGGAGCAGGAGAATCACCT

GCCAGAGAGACCGACGAATGATCAAGCCTCCTAA

The amino acid sequence of PP2CABA (long form, L) is shown below:

SEQ ID NO: 2
mrevlllgslvvlallslfpccsclsqgaeeeeddgevrlmglageaags pgsgggfsangkfsygyasspgkrssmedfydtridgvdgetvglfgvfd ghggaraaefvkqnlftnlikhpklfsdtksaiaetytstdsellkaets hnrdagstastailvgdrllvanvgdsravicrggdaiavsrdhkpdqsd erqriedaggfvmwagtwrvggvlavsrafgdkllkqyvvadpeikeevv dssleflilasdglwdvvtneeavamvkpildseqaakkllqeasqrgsa dnitclvvrfleqenhlperptndqas The nucleotide sequence of PP2CABA (short form, S) is shown below:

SEQ ID NO: 3
ATGGGGCTCGCCGGAGAGGCCGCTGGCTCGCCTGGCAGTGGCGGCGGGTT

CAGTGCAAATGGTAAATTTAGCTATGGTTATGCGAGCTCTCCTGGAAAAA

GATCCTCCATGGAGGACTTCTATGACACCAGAATTGATGGTGTCGATGGA

GAGACCGTTGGACTGTTTGGTGTCTTTGATGGTCATGGTGGAGCTCGAGC

AGCAGAATTCGTCAAGCAGAACCTCTTCACCAATTTAATCAAGCACCCAA

AGTTATTCAGTGATACCAAGTCTGCAATTGCTGAAACTTACACTAGCACG

GACTCTGAACTTCTGAAAGCTGAAACCAGCCACAATCGAGATGCAGGGTC

GACTGCCTCCACTGCAATTCTCGTAGGCGACCGTCTGCTCGTTGCAAATG

TTGGAGATTCTAGGGCTGTCATTTGTAGAGGAGGAGATGCTATAGCTGTG

TCAAGAGACCACAAGCCTGATCAGTCAGACGAGAGGCAGAGGATAGAGGA

TGCTGGTGGTTTTGTGATGTGGGCTGGAACATGGCGCGTGGGTGGTGTTC

TTGCTGTCTCTCGAGCATTTGGTGACAAACTCCTGAAGCAATATGTGGTT

GCTGATCCAGAGATCAAGGAGGAGGTGGTCGACAGCTCTCTCGAGTTCCT

CATCCTTGCTAGTGATGGCCTCTGGGACGTGGTGACCAACGAGGAAGCTG

TGGCCATGGTGAAGCCAATTCTGGATTCAGAGCAGGCTGCAAAGAAGCTC

CTCCAGGAGGCCTCACAGAGGGGAAGCGCAGACAACATCACCTGCCTCGT

CGTCCGTTTCTTGGAGCAGGAGAATCACCTGCCAGAGAGACCGACGAATG

ATCAAGCCTCCTAA

Figure 4A:
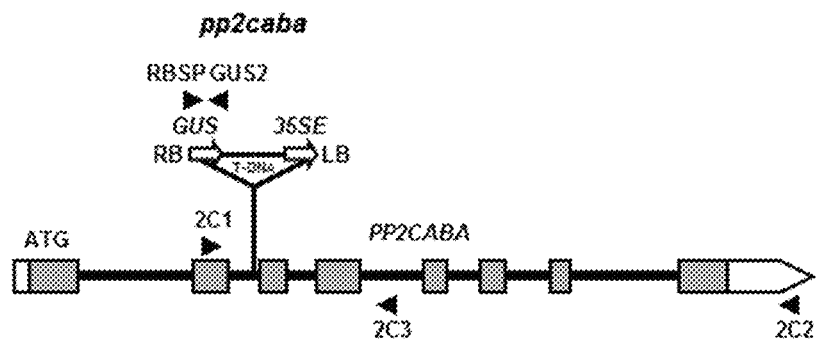
FIG. 4A to FIG. 4C include diagrams showing identification of rice pp2caba mutant.
Figure 4B:
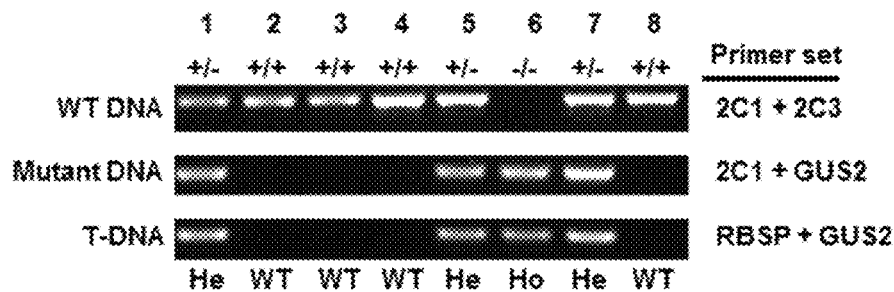
Figure 4C:
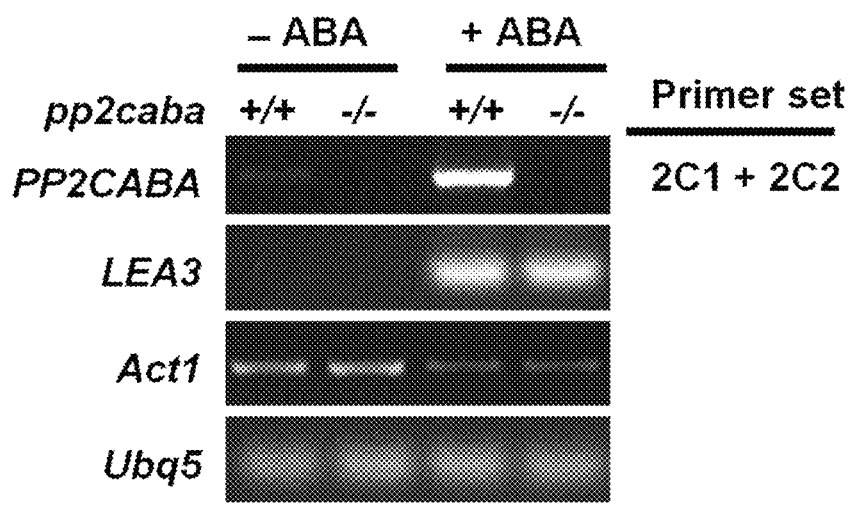
Figure 5A:
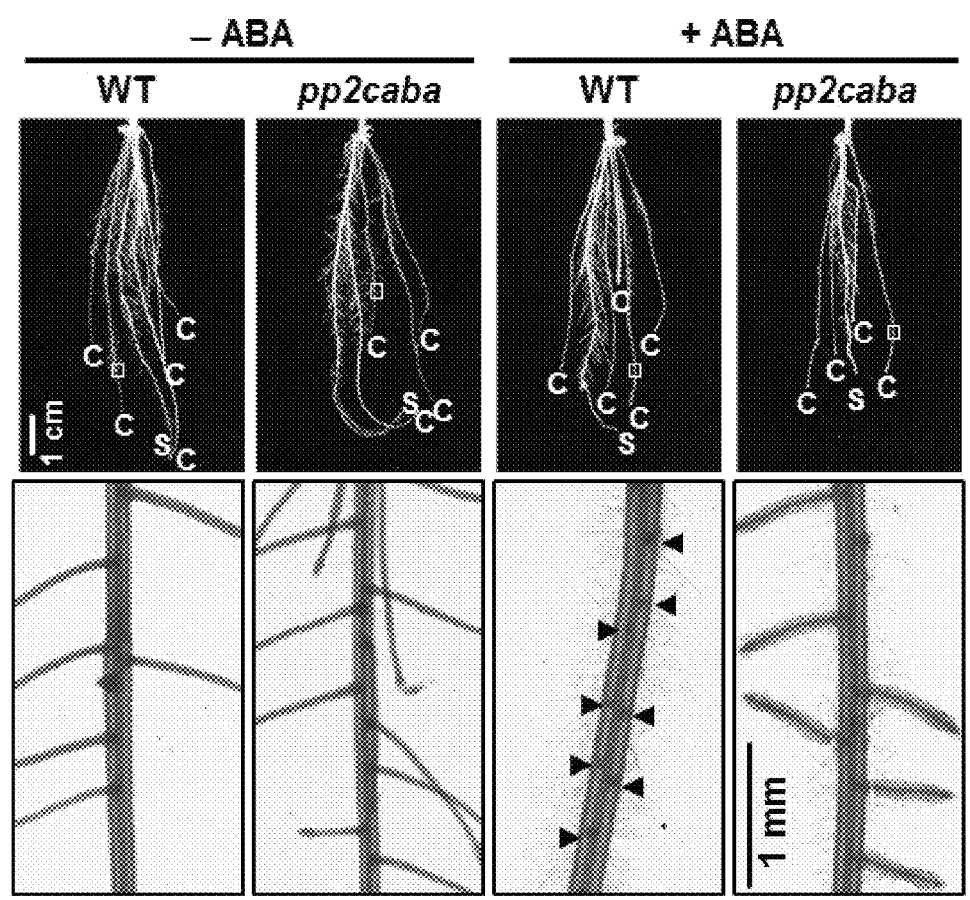
FIG. 5A to FIG. 5B include photos showing plants have lower LR to PR ratio under induction of ABA and expression of PP2CABA.
Figure 5B:
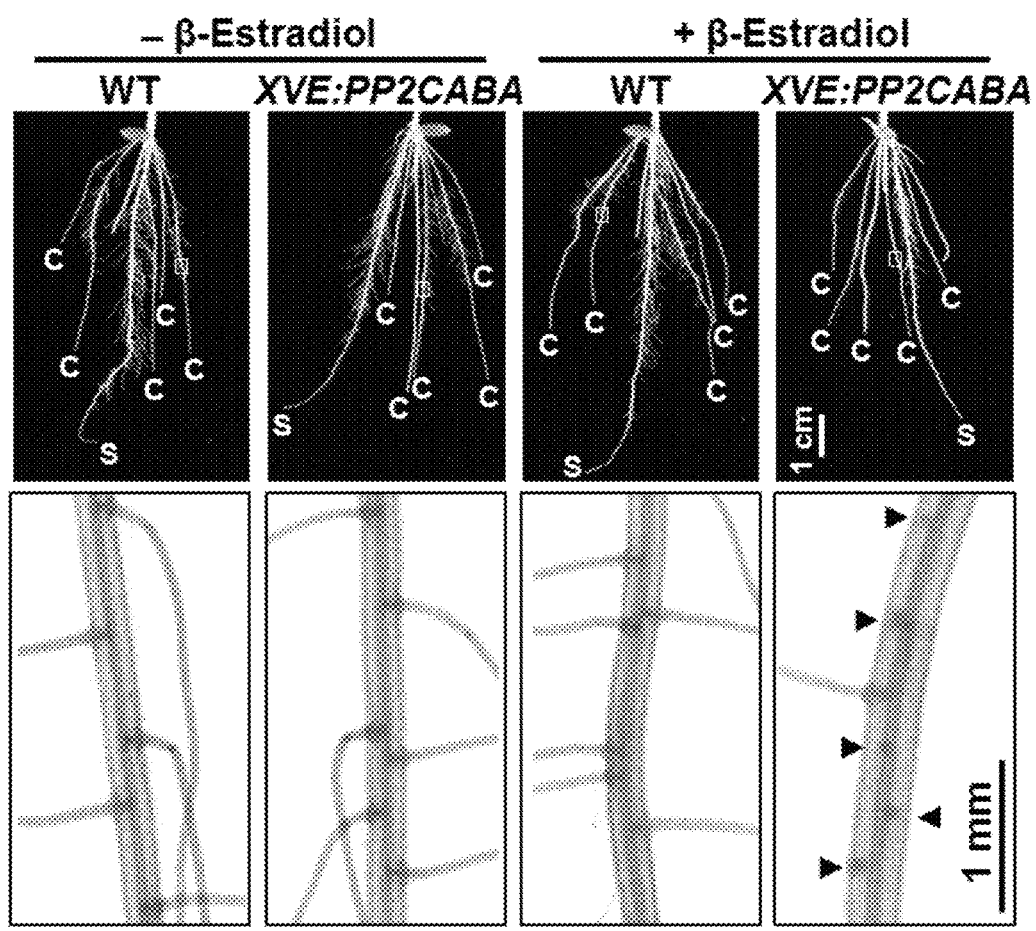

The amino acid sequence of PP2CABA (short form, S) is shown below:

SEQ ID NO: 4
Mglageaagspgsgggfsangkfsygyasspgkrssmedfydtridgvdg etvglfgvfdghggaraaefvkqnlftnlikhpklfsdtksaiaetytst dsellkaetshnrdagstastailvgdrllvanvgdsravicrggdaiav srdhkpdqsderqriedaggfvmwagtwrvggvlavsrafgdkllkqyvv adpeikeevvdssleflilasdglwdvvtneeavamvkpildseqaakkl lqeasqrgsadnitclvvrfleqenhlperptndqas Characterization of the Impact of ABA and PP2CABA on LR Elongation To investigate the function of PP2CABA in rice, a T-DNA-tagged gene knockout rice mutant pp2caba was obtained from the Taiwan Rice Insertional Mutant (TRIM) population. The T-DNA is inserted in the second intron, 816 bp downstream of the translation start codon (FIG. 4A). Genotyping identified segregated WT, heterozygous and homozygous pp2caba mutant (FIG. 4B). PP2CABA transcripts were absent in the homozygous plant, indicating that PP2CABA is a loss-of-function mutant (FIG. 4C). Since the PP2CABA promoter is active in roots and induced by ABA, the development of roots in PP2CABA in response to ABA was examined. Without ABA, no difference in LR growth was detected between WT and pp2caba seedlings, but with 1 µM ABA which is known to suppress rice LR growth (Chen et al., Plant Biotechnol J, 13:105 (2015)), the root diameter was enlarged and LR growth was completely inhibited in WT and stunted in pp2caba in maturation zones of roots (FIG. 5A). The root diameter was enlarged in roots treated with ABA in both WT and pp2caba. The reduced LRP growth in WT caused by ABA was due to inhibition of LR elongation instead of LRP initiation. To confirm that PP2CABA suppresses LR growth, a construct containing the coding sequence of PP2CABA fused to a double HA epitope under the control of a β-estradiol-inducible XVE promoter (Zuo et al., Methods Mol Biol, 323:329 (2006)) was introduced into the rice genome. Without β-estradiol induction, no difference in LR growth was detected in seedlings between transgenic rice and WT; in contrast, with β-estradiol induction, LR and crown root growth was reduced but the root diameter was enlarged in transgenic rice (FIG. 5B). The reduced LR growth in the PP2CABA-overexpressing line was also due to inhibition of LR emergence instead of LRP initiation (FIG. 5B).

Figure 6D:
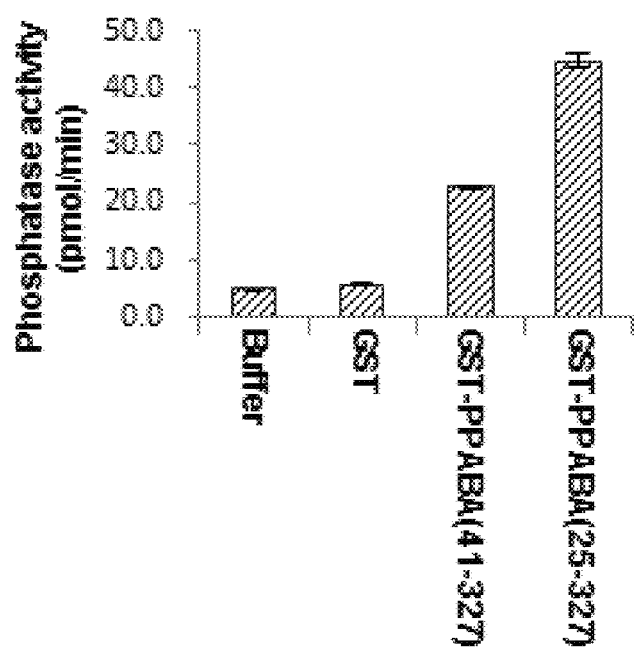
Figure 6E:
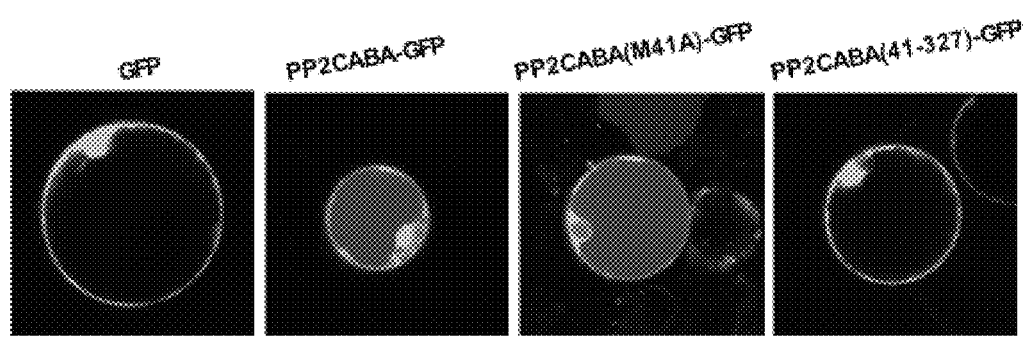
Figure 7A:
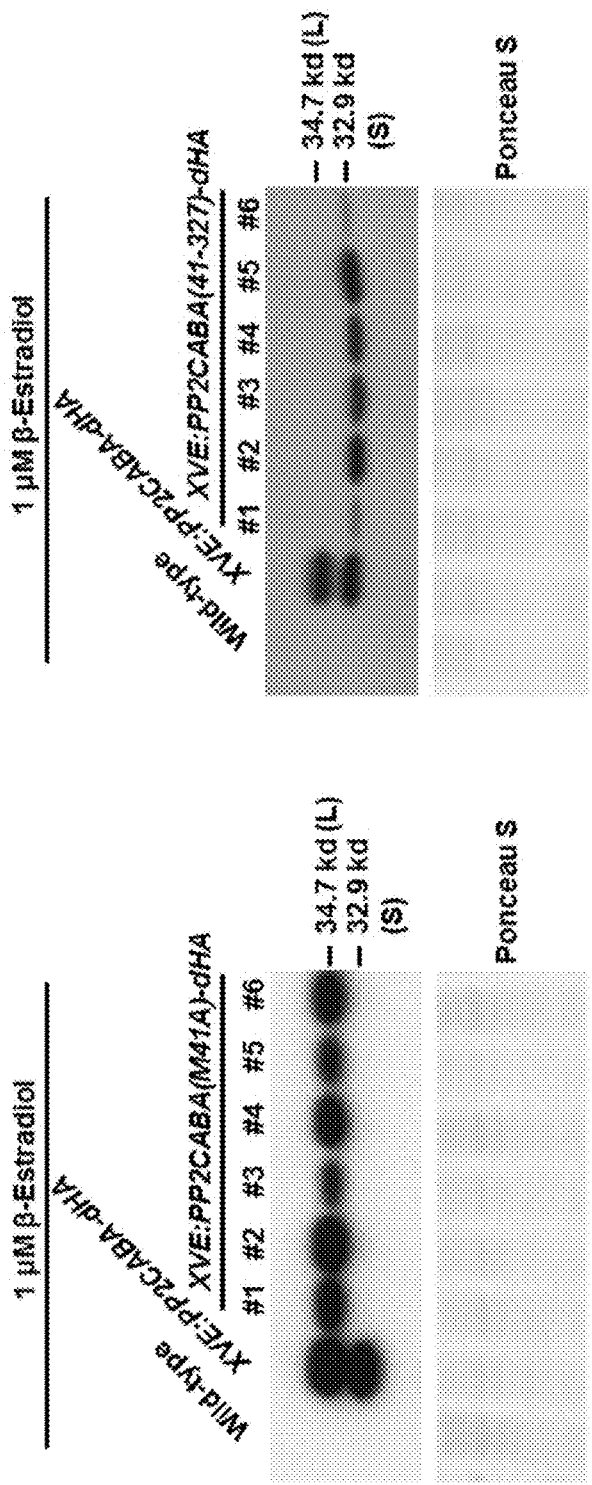
FIG. 7A to FIG. 7B includes diagrams showing PP2CABA short form having a lower degree of lateral root growth.
Figure 7B:
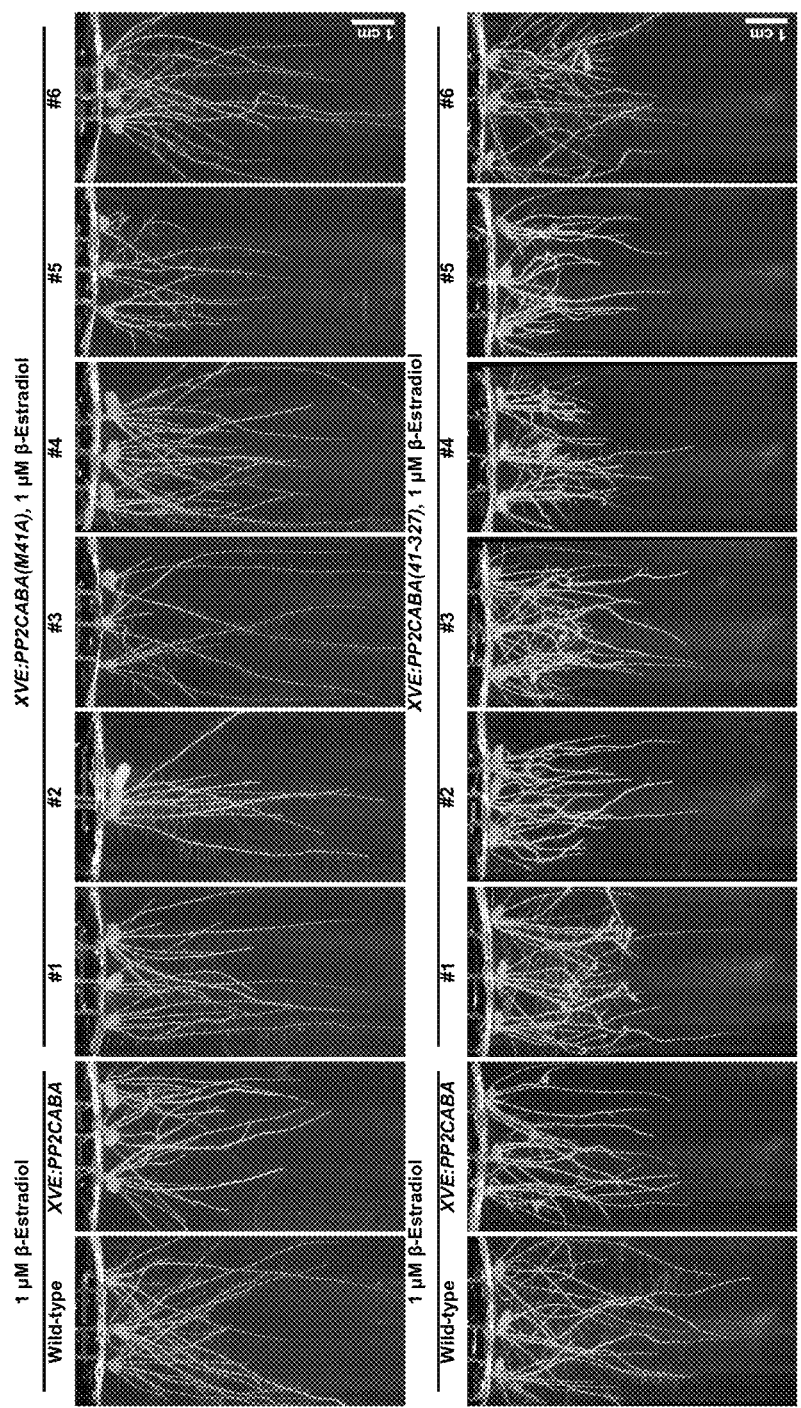

Bioinformatics analysis with the SMART program (smart.embl-heidelberg.de/) predicted a canonical signal peptide at the N-terminus region (amino acids 1-24) and a PP2C catalytic domain (amino acids 54-308) in the PP2CABA protein (FIG. 6A). Western blot analysis revealed two forms of endogenous PP2CABA in WT dry embryos (FIG. 6B). Overexpression of double HA-tagged PP2CABA in protoplasts also showed the presence of two translational products (FIG. 6C). A mutated version of PP2CABA-dHA, PP2CABA(M41A)-dHA, was generated in which the second ATG codon is mutated to GCT codon, resulted in the replacement of the 41$^{st}$ amino acid residue methionine with alanine. Only PP2CABA(L) was detectable in protoplasts transfected with PP2CABA(M41A)-dHA (FIG. 6C). A truncated version of PP2CABA-dHA, PP2CABA(41-327)-dHA, was also generated in which the coding sequence of PP2CABA at 5' of the second ATG codon was deleted. Only PP2CABA(S) was detectable in protoplasts transfected with PP2CABA(41-327)-dHA (FIG. 6C). These results indicate that the long (L) form translated from the 1$^{St}$ ATG and the short (S) form translated from the 2$^{nd}$ ATG (Met at amino acid residue 41) of cDNA, with predicted molecular weights of 32.4 and 30.6 kd, respectively. Protein phosphatase activity analysis shows both of L form and S form of PP2CABA have phosphatase activities which can remove the phosphate from the synthetic phosphopeptide (FIG. 6D). Transient expression analysis of PP2CABA fused to GFP in rice protoplast showed that the L form was present in endomembranes and vacuole and S form in nucleus and cytoplasm (FIG. 6E). To determine which of the two forms of PP2CABA is responsible for inhibition of LR emergence, transgenic rice containing XVE:PP2CABA(M41A)-dHA or XVE:PP2CABA(41-327)-dHA were generated, and expression level of two forms of PP2CABA in roots were examined (FIG. 7A). Overexpression of long form PP2CABA (M41A)-dHA did not inhibit, whereas short form PP2CABA (41-327)-dHA did inhibit LR emergence in a dose dependent manner (FIG. 7B). These results indicate that the short form PP2CABA is sufficient to induce the ABA-mediated suppression of LR elongation.

Figure 8A:
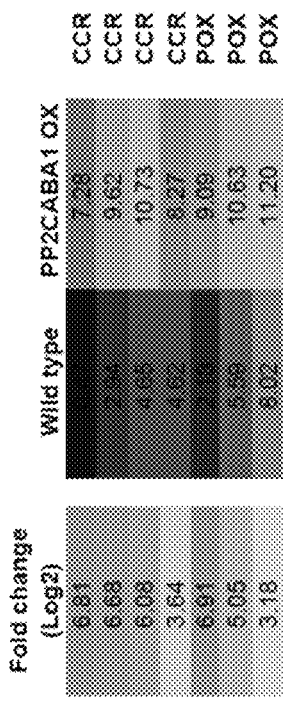
FIG. 8A to FIG. 8B include diagrams showing PP2CABA up-regulating the expression of genes essential for lignin and suberin biosynthesis.
Figure 8A:
Figure 8A:
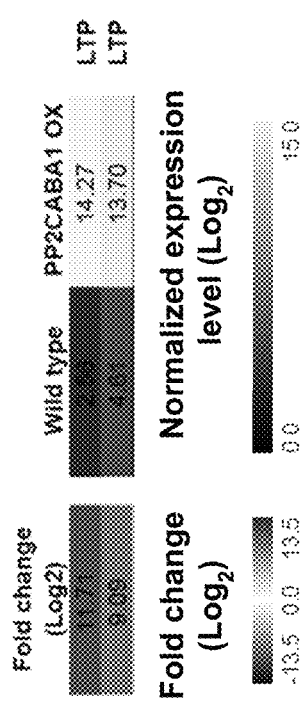

Characterization of the Impact of ABA and PP2CABA on Lignin and Suberin Biosynthesis in Root Periphery Tissues To understand the molecular mechanism of inhibition of root growth by PP2CABA, the genome-wide expression profiles in PP2CABA-overexpressing and WT roots were first compared. A total of 654 genes were up-regulated and 669 genes were down-regulated by more than 4-fold changes by PP2CABA as compared with WT. Then, the putative function of these PP2CABA-regulated genes was analyzed with a gene ontology database GOEAST (world wide web (www) link: omicslab.genetics.ac.cn/GOEAST/). Many PP2CABA up-regulated genes seem to be over-presented for functions in metabolism, therefore, they were further analyzed with the KEGG database (world wide web (www) link: genome.jp/kegg/pathway.html). Many PP2CABA highly up-regulated genes were classified in groups for functions in phenylpropanoid biosynthesis, fatty acid elongation and lipid transfer (FIG. 8A).

Figure 8B:
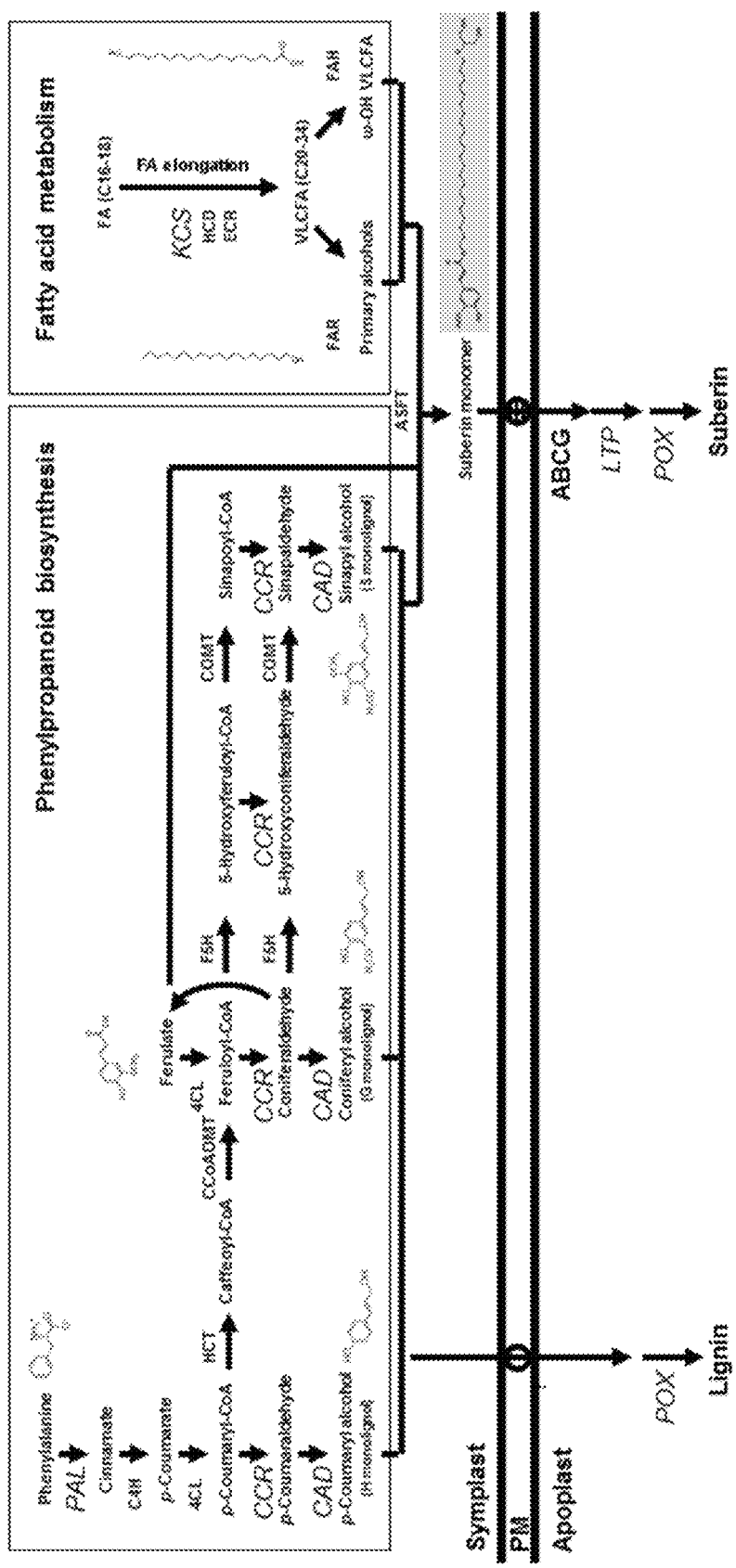
Figure 9A:
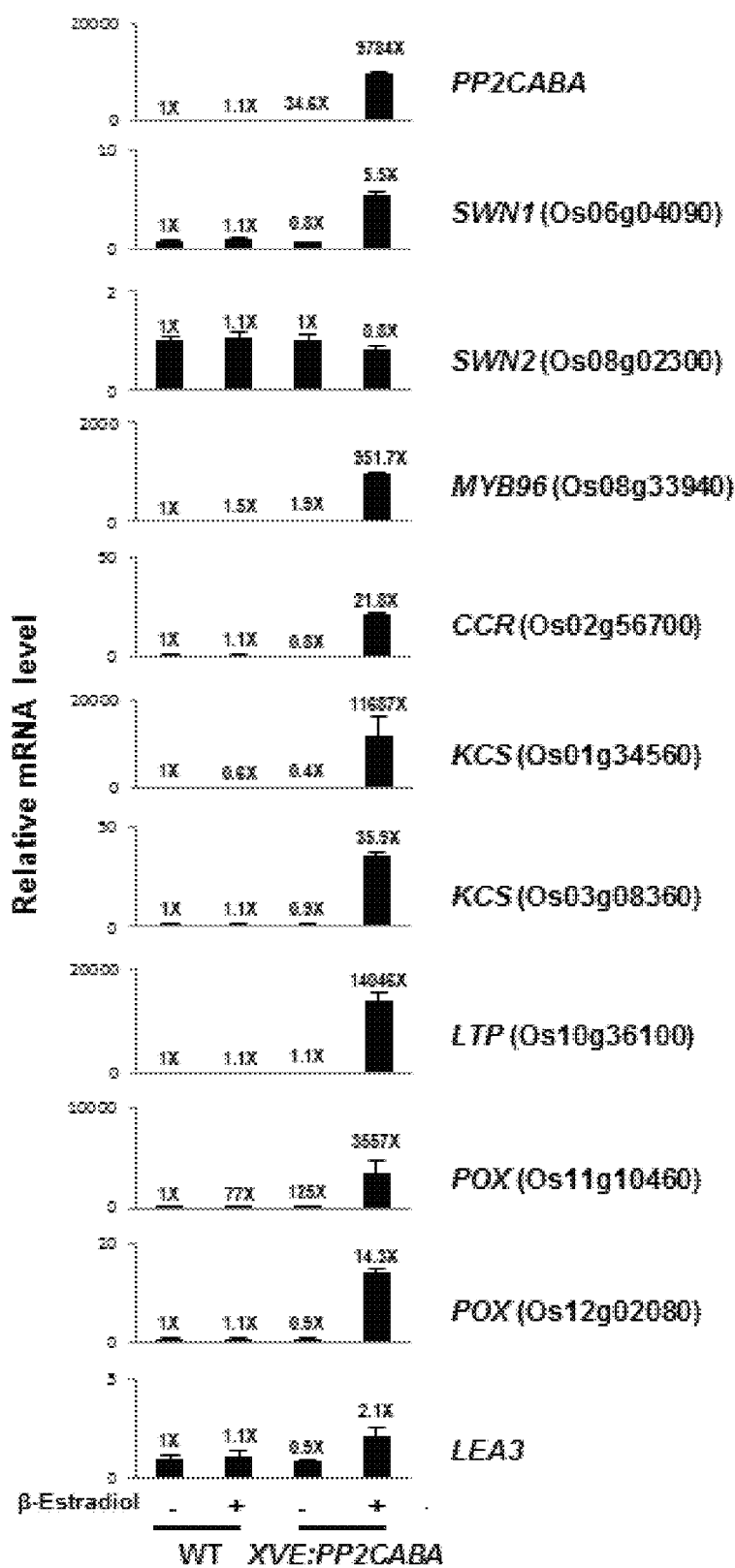
FIG. 9A to FIG. 9B include diagrams showing that ABA and PP2CABA up-regulating the expression of genes essential for lignin and suberin biosynthesis.
Figure 9B:
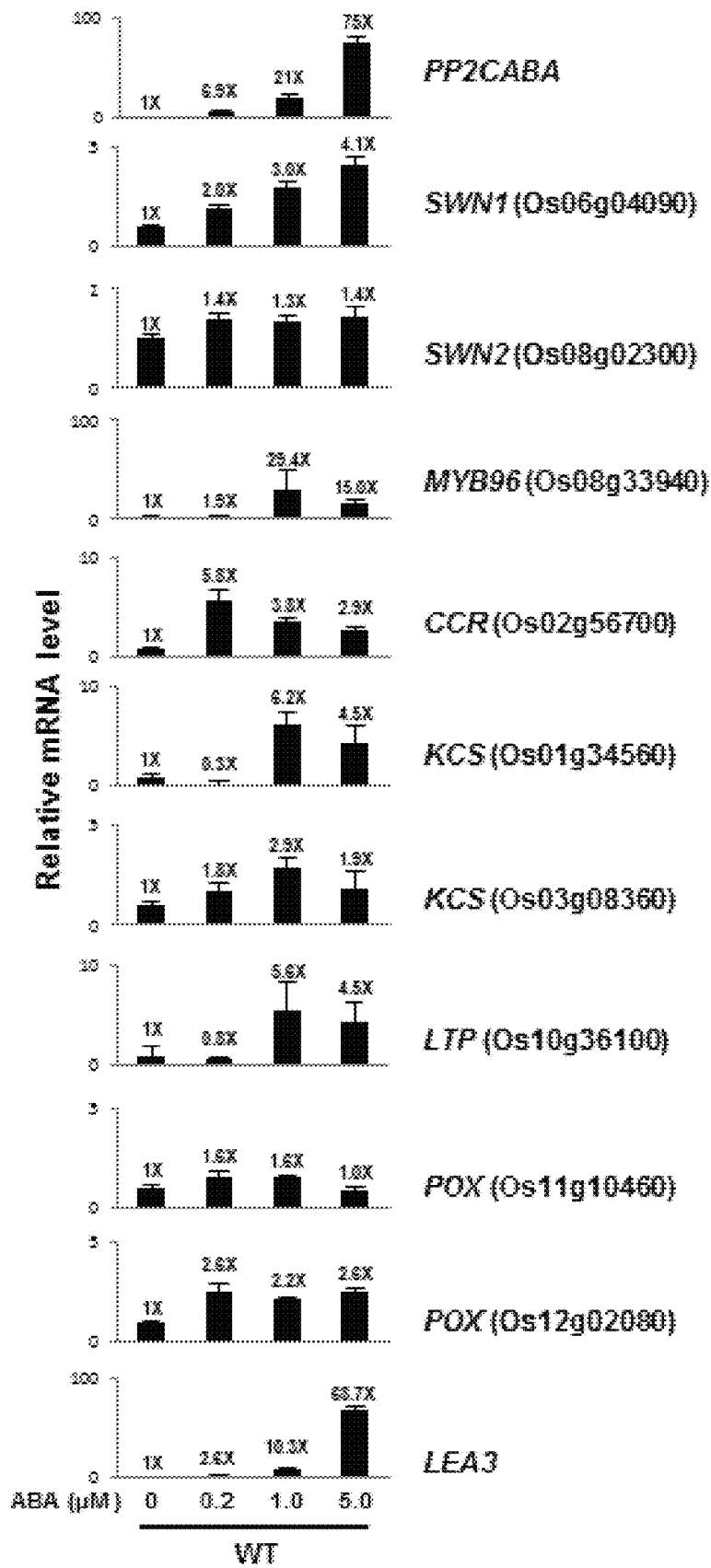

The lignin and suberin biosynthesis in plants shares the phenylpropanoid biosynthesis pathways which result in the production of monolignols and ferulate (Cabane et al., Lignins: Biosynthesis, Biodegradation and Bioengineering, 61:219 (2012)). Lignin polymers are finally synthesized through the oxidative polymerization of monolignol in apoplast (Bonawitz et al., Annual Review of Genetics, 44:337 (2010)) (FIG. 8B). Suberin is a complex acylglycerol polymer composed of very long chain fatty acid, ferulate and glycerol (Beisson et al., Current Opinion in Plant Biology, 15:329 (2012)). Mono- and oligomeric suberin precursors are exported to the apoplast by the subfamily GABC transporters (ABCG) (Landgraf et al., Plant Cell, 26:3403 (2014); Shiono et al., Plant J, 80:40 (2014); Yadav et al., Plant Cell, 26:3569 (2014)), across the cell wall by lipid transfer proteins (LTP) (Pollard et al., 2008), and finally polymerized by the cell wall class III peroxidases (POX) (Beisson et al., 2012) (FIG. 8B). The results revealed that the accumulation of mRNA of phenylalanine ammonia lyase (PAL), the first enzyme in the phenylpropanoid pathway, Cinnamoyl-CoA reductase (CCR) and cinnamyl alcohol dehydrogenase (CAD) essential for formation of monolignol, 3-ketoacyl-CoA synthase (KCS) required for formation of very long chain fatty acids, lipid transfer proteins (LTP) which exports suberin monomer in apoplast, and class III peroxidase (POX) which polymerizes the monomeric building blocks into lignin and suberin macromolecule (Cabane et al., Lignins: Biosynthesis, Biodegradation and Bioengineering, 61:219 (2012)) were significantly enhanced by overexpression of PP2CABA (FIG. 8A). The expression of transcription factors SWN1 necessary for thickening of sclerenchyma cell walls In rice (Yoshida et al., Frontiers in plant science, 4:383 (2013)) and MYB96 essential for biosynthesis of cuticular wax and suberin in *Arabidopsis* (Seo et al., Plant Cell, 23:1138 (2011)) are also increased by PP2CABA. Quantitative RT-PCR analysis confirmed that the expression of these genes is up-regulated by PP2CABA in rice roots (FIG. 9A). Expression of these genes was also induced by ABA in WT, except PAL and CAD, but in much reduced scales compared with the PP2CABA-overexpressing line (FIG. 9B).

Figures 10A, 10B:
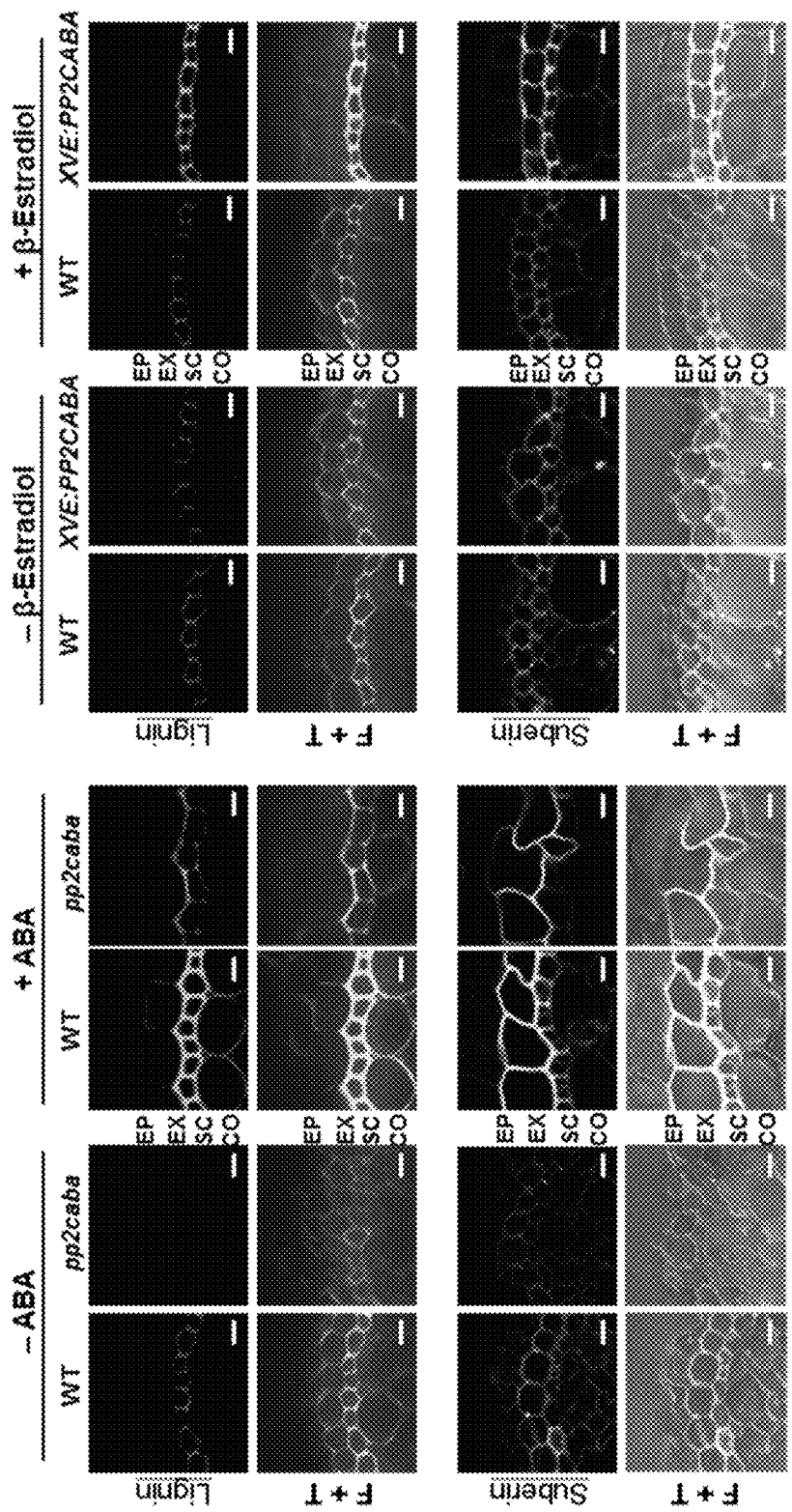
FIG. 10A to FIG. 10B include photos showing ABA and PP2CABA enhance the accumulation of lignin and suberin in cell walls of root peripheral layers and increase the root diameter.

To determine whether the up-regulation of genes involved in the phenylpropanoid metabolism implies changes in cell wall modification in roots, it was further examined whether PP2CABA is sufficient and necessary for ABA-induced lignification and suberization in cell walls of roots. Acriflavin staining for lignin and fluorol yellow staining for aliphatic suberin (Landgraf et al., Plant Cell, 26:3403 (2014); Rocha et al., Front Plant Sci, 5:102 (2014)) were performed in root sections. ABA and PP2CABA enhanced the accumulation of lignin and suberin in endodermal and exodermal cell layers in roots. Detailed examination of these cell layers revealed that lignin is present mainly in peripheral sclerenchyma and suberin mainly in exodermis and sclerenchyma in WT, whereas the accumulation of lignin and suberin disappeared in these tissues in pp2caba (FIG. 10A, left panel). ABA enhanced the accumulation of lignin in same tissues, and to higher extent in WT than in pp2caba (FIG. 10A, right panel). β-estradiol enhanced the accumulation of lignin in XVE:PP2CABA transgenic line as compared with WT (FIG. 10B, right panel). ABA and PP2CABA also enhanced the accumulation of lignin in LRP in WT and XVE:PP2CABA transgenic line, respectively, and to a suppression of LR growth by ABA and PP2CABA higher extent than in pp2caba treated with ABA.

Figure 11:
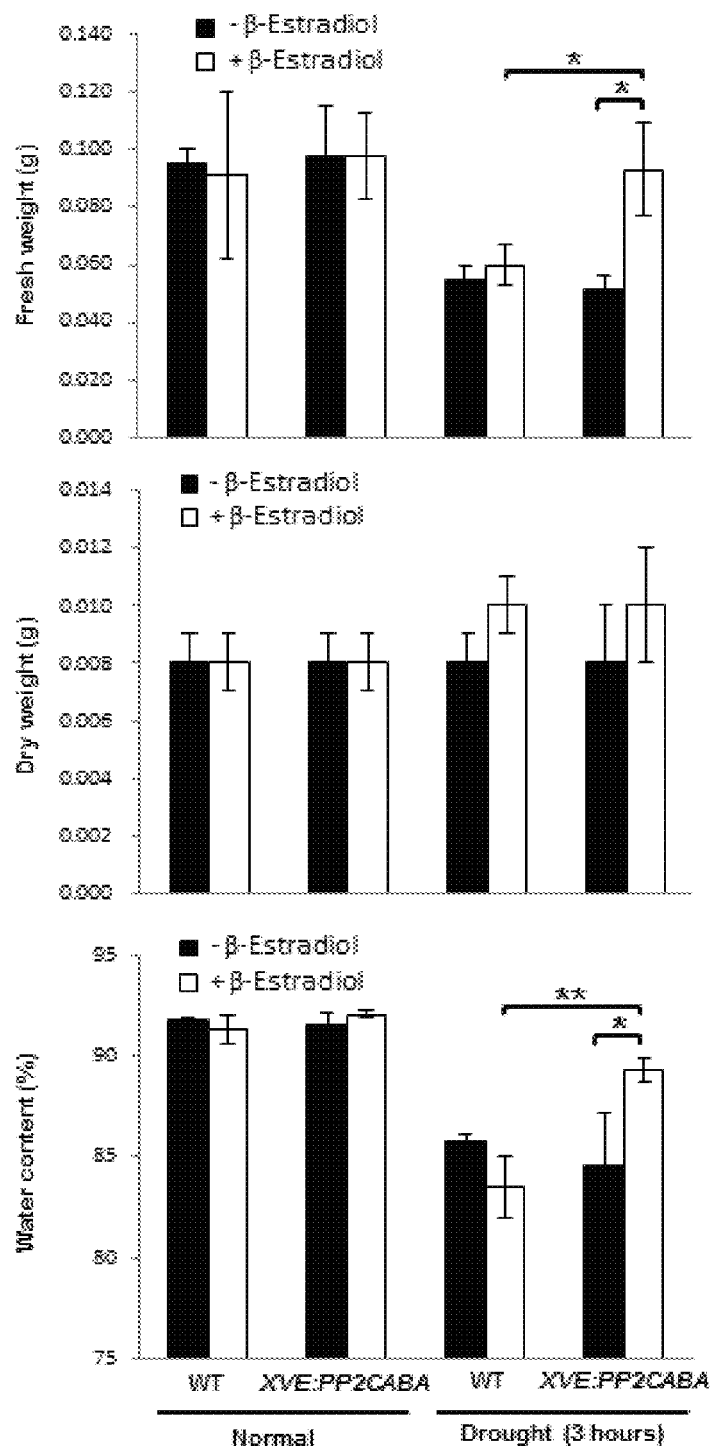
FIG. 11 include charts showing overexpression of PP2CABA increases water holding capability in roots. Three-day-old seedlings of WT and transgenic rice carrying XVE:PP2CABA-dHA were treated with or without 3 µM β-Estradiol for 4 days. Those seven-day-old plants were then treated with or without 3 hour dehydration on paper towels. Roots were collected for fresh weight (FW) measurements (top panel). Dry weight (DW) were measured after dried in a 65 degree C. oven for 18 hours. Water content (%) were calculated by (FW−DW)/FW×100 (middle panel). Water content is shown in the bottom panel.
Figure 12B:
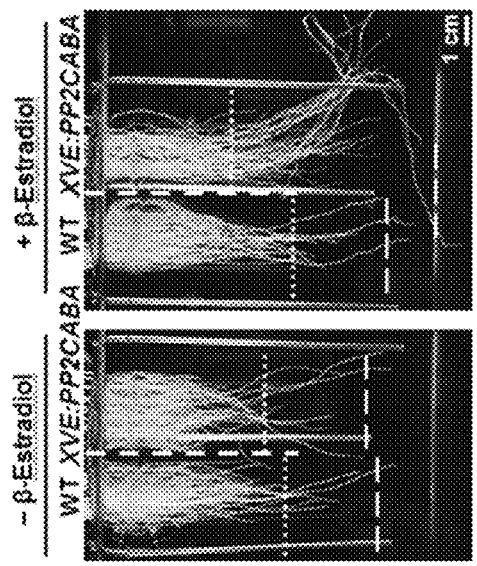
FIG. 12A to FIG. 12C include photos showing PP2CABA-priming has higher osmotic stress tolerance.
Figure 12A:
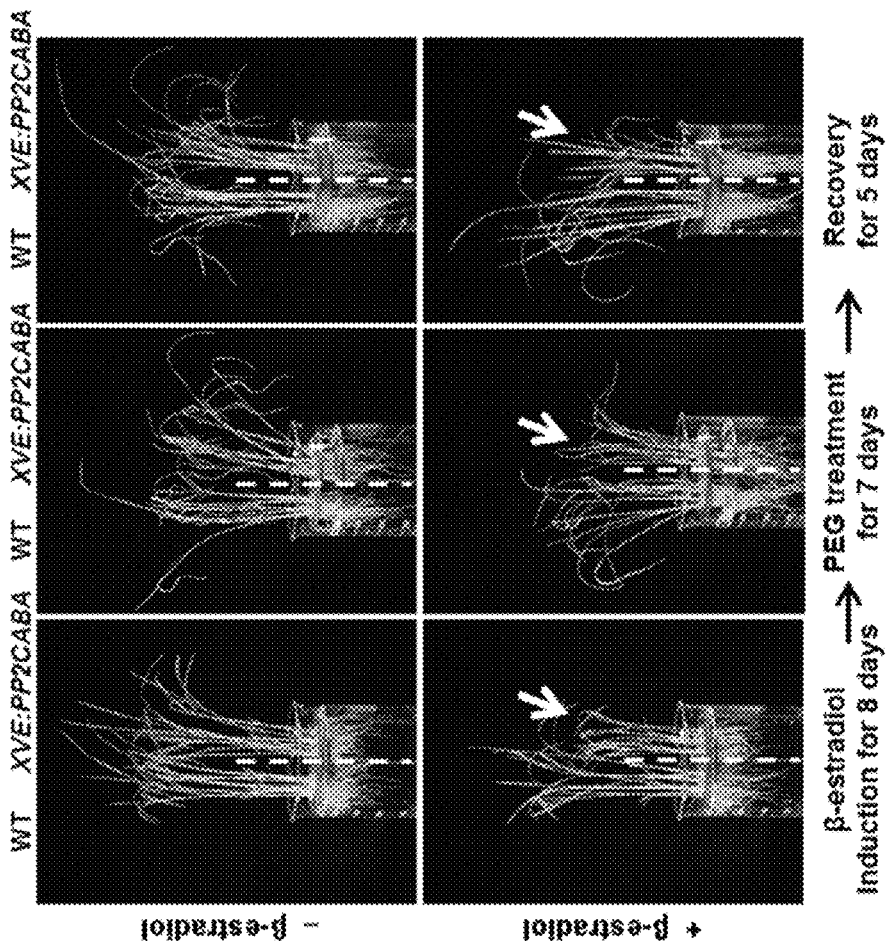

Characterization of the Impact of PP2CABA-Priming on Leaf Damage and Root Growth under Osmotic Stress Suberin in exodermis has been proposed to form a barrier to water movement through the root apoplast. Elevated accumulation of suberin in PP2CABA-overexpressing roots may reinforce the lipid barrier, leading to reduction of water loss from root back to the outside environment. To test this hypothesis, a water holding ability analysis was performed. XVE:PP2CABA transgenic plants were pre-treated with or without β-estradiol for 4 days, a process of PP2CABA-priming. β-Estradiol was removed and seedlings were then treated with or without dehydration for 3 hour on paper towels. Roots of PP2CABA-primed plants obviously keep more water than WT and PP2CABA-non-primed plants (FIG. 11). This result indicate that overexpression of PP2CABA increases the formation of diffusion barriers in roots leading to increases its water holding capability. An osmotic stress tolerance analysis was also performed. XVE:PP2CABA transgenic plants were pre-treated with or without β-estradiol in hydroponic solution for 8 days, the shoot and root length of PP2CABA-overexpressing seedlings were shorter than WT (FIG. 12A, left panel). β-Estradiol was removed and seedlings were then treated with 20% polyethylene glycol (PEG), which is equivalent to −0.7 MPa, for 7 days; leaves of WT and PP2CABA-non-primed plants were wilted but of PP2CABA-primed plants remained unwilted and straight (FIG. 12A, middle panel). After recovery in hydroponic solution without PEG, leaves of PP2CABA-primed plants remained unwilted while those of WT and PP2CABA-non-primed plants were severely wilted at leaf tips (FIG. 12A, right panel). In the 20% PEG solution, LR and PR of PP2CABA-primed plants continued to grow faster than those of WT, pp2caba and PP2CABA-non-primed roots (FIG. 12B).

Figure 12C:
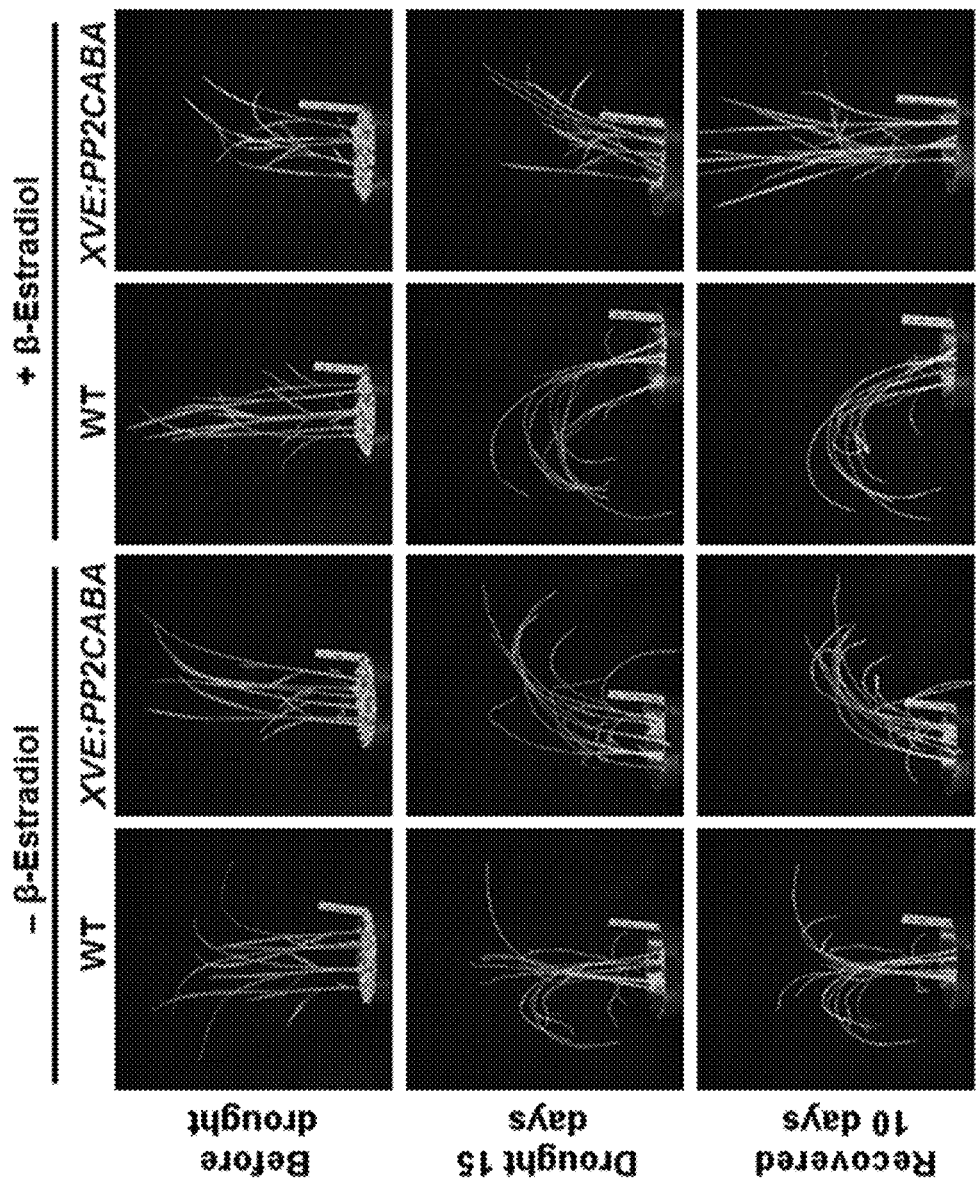

The drought stress tolerance of plants was also tested by growing plants in vermiculite. Leaves of WT and XVE:PP2CABA line without β-estradiol induction were wilting (drying and drooping in appearance), but those of XVE:PP2CABA line with β-estradiol induction were growing well (rigid and straight in appearance), after water withholding for 15 days or recovery with hydroponic solution (FIG. 12C). These studies demonstrate that PP2CABA priming leads to acclimation of plants against osmotic stress.

Characterization of the Impact of PP2CABA on LR Elongation and Cell Modifications in LRP and Peripheral Root Tissues Drought stress is one of the major constraints limiting plant growth and productivity and resulting in significant economic losses worldwide. Understanding mechanisms by which plants response to drought stress and regulate root architecture is of great agronomic significance for the development of efficient breeding programs for stress tolerant varieties. Here, an abiotic stress-inducible protein phosphatase PP2CABA that regulates an adaptive mechanism for plant to survive, by modifying root architecture and avoiding excess water loss, under water deficit conditions was identified.

Root growth could be enhanced or suppressed depending on soil water contents, which offers one of the major acclimation strategies for plants to adapt to water limitation in soil. The development of root architecture is sensitive to and tightly regulated by micro-scale changes of water availability in soil. In rice, low ABA concentrations ($\leq 0.1$ µM) enhance while higher concentrations ($\geq 0.2$ µM) inhibit LR growth, with higher concentrations of ABA exhibiting greater inhibition, and enlarges PR thickness (Chen et al., Plant Biotechnol J, 13:105 (2015)). Consequently, ABA treatments mimic low water potentials or osmotic stress in dehydrated soils, with low concentrations inducing root system for increasing root surface for more efficient water uptake, while high concentrations arrest root branching but promote mechanical strength and allow continued PR growth to facilitate water uptake from deep soil.

The results disclosed herein further show that LR growth was more severely inhibited in WT than in pp2caba mutant by 1 µM ABA, and in PP2CABA-overexpressing plants than in WT in the absence of ABA. The suppression of LR growth by ABA and PP2CABA resulted from inhibition of LR elongation instead of LRP initiation (FIG. 5A). The expression of PP2CABA was mainly induced by ABA at concentrations $\geq 0.2$ µM (FIG. 3B), further indicating that PP2CABA plays a key role in sensing the ABA signaling in suppression of LR growth.

In drying soil, root cells must activate processes to limit water loss and mitigate its harmful effects. Roots respond to water limitation by modification of cell walls in endodermis and exodermis for the formation of apoplastic barriers that prevent water loss to the soil (Cabane et al., Lignins: Biosynthesis, Biodegaradation and Bioengineering, 61:219 (2012); Enstone et al., J Plant Growth Regul, 21:335 (2003a); Moura et al., J integr Plant Biol, 52:360 (2010); Ranathunge et al., Plant Science, 180:399 (2011)), and ABA can enhance suberization in *Arabidopsis* roots, potato tubers and tomato stem scar (Cottle et al., Plant Physiology, 70:775 (1982); Efetova et al., Plant Physiology, 145:853 (2007); Leide et al., New Phytol, 194:402 (2012)). However, the mechanism that regulates the process of cell wall modification in peripheral tissues in roots remains mostly unclear.

The results disclosed herein show that PP2CABA plays a key role in mediating the ABA signaling in up-regulation of genes essential for lignin and suberin biosynthesis in rice. It is not only necessary for the development of secondary cell walls in specialized cell layers under normal growth but also sufficient to reinforce the function of secondary cell walls in response to ABA and abiotic stress in rice roots (FIG. 10A). In pp2caba, the accumulation of lignin and suberin was abolished under normal growth conditions, but remained in the presence of ABA, indicating additional gene(s) also regulates the biosynthesis of these chemicals in response to ABA. Most enzymes of phenylpropanoid biosynthesis pathways are encoded by multigene families, but only certain members are involved in the synthesis of constitutive lignin under normal growth whereas others specifically function in response to biotic and abiotic stresses (Cabane et al., Lignins: Biosynthesis, Biodegradation and Bioengineering, 61:219 (2012)). As also shown herein, only some members of a gene family and not all families involved in the biosynthesis of lignin and suberin were highly activated by ABA and PP2CABA. It is unclear how these genes are differentially regulated by ABA and PP2CABA.

The inhibition of LR growth in ABA-treated or PP2CABA-overexpressed roots could have resulted from two mechanisms. First, the thickening of walls in peripheral cell layers at the differentiation and maturation zones of roots in ABA-treated WT and PP2CABA-overexpressing lines inhibits LRP emergence when they reached these thickened cell layer (FIG. 5A and FIG. 5B). The notion is supported by a study in rice showing that sulphide treatment of soil triggers suberization and thickening of walls within the exodermis and epidermis of roots, in which cortex walls are not modified and LR growth is not affected when it passes through the cortex; however, when the LR reaches the two outermost tissues, the progression of LRP toward the rhizosphere is blocked (Armstrong et al., Ann Bot, 96:625 (2005)). Second, the LRP undergoes extensive lignification in ABA-treated WT and PP2CABA-overexpressing roots, which may restrict the extension of LRP.

Growth of a root occurs through cell expansion in the elongation zone and is sustained by cell divisions in the meristem. In maize seedlings, maintenance of cell wall extensibility in the apical part of roots, by increase in expansin activity and loosening in cell wall structures by enzymes such as xyloglucan endotransglycosylase and glucanase, for continued root elongation, has been considered as an important strategy for adaptation to low water potential (Wu et al., J Exp Bot, 51:1543 (2000)). The PP2CABA-GUS is expressed mainly in maturation zone (FIG. 3D). Additionally, LR growth in the differentiation and maturation zones were inhibited in the ABA-treated WT and PP2CABA-overexpressing roots, but no difference in the accumulation of lignin and suberin in apical 2-3 mm of the rice roots was detected. This observation explains the continuous growth of PR in PP2CABA-overexpressing lines treated with PEG (FIG. 12B).

Characterization of the Impact of PP2CABA-Priming on Acclimation of Plants to Osmotic Stress Tolerance The biochemical and anatomical changes in root peripheral cell layers induced by ABA and PP2CABA provide a water conservation measure to protect roots from water loss in the high osmotic stress condition. PP2CABA enhances the ABA-dependent accumulation of lignin in LRP, leading to inhibition of LR elongation that is supposed to prevent the formation of gaps on root surface at sites of later root emergence (Peret et al., Journal of Experimental Botany, 60:3637 (2009a)). PP2CABA also enhances the accumulation of lignin and suberin in cell walls of root peripheral tissues, which form a waterproof layer (Enstone et al., Journal of Plant Growth Regulation, 21:335 (2003b)). These modified root structures may reduce the root surface area for water uptake from the soil, however, they may strengthen cell walls for improved mechanical support of the plant aerial structure as well as water transport, and limit apoplastic transport of water to allow a higher degree of ion selectivity in the case of salt stress and to impede water loss to the soil, under water deficit conditions (Cabane et al., Lignins: Biosynthesis, Biodegradation and Bioengineering, 61:219 (2012)). In maize seedlings, seminal roots develop extensive suberization in both the endo- and exodermal layers under drying stress, root tips remain alive throughout the stress period, and upon rehydration, the existing roots of the surviving seedlings recommence elongation (Stasovski et al., Can J Bot, 69:1170 (1991)). Consequently, the PP2CABA-medaited cell wall modification in LRP and peripheral root tissues seems to be a dilemma, these measures offer acclimation strategies for plants to resist desiccation under salt and drought stress conditions. This notion is supported by the significantly enhanced osmotic and drought stress tolerance in plants with PP2CABA-priming in advance (FIG. 12A to FIG. 12C). Additionally, retarded shoot and LR growth but enhanced root diameter by ABA or overexpression of PP2CABA may conserve water, minerals and sugars that favor reallocation of carbon sources to other defense mechanisms or facilitate regrowth of primary roots after relief from stress conditions.

Many members of PP2Cs mediate abiotic stress-triggered signaling pathways, and most studies have been focused on Glade-A PP2Cs that negatively regulate the ABA-invoked physiological responses through the PYR/PYL/PCAR-SnRK2-dependent pathway, such as the inhibition of germination and root growth or stomatal closure in *Arabidopsis* (Fuchs et al., The FEBS journal, 280:681 (2013)). Clade F2-PP2Cs are less studied but also shown to play various roles in plant stress response and growth, such as the *Arabidopsis* WIN2 enhances resistance to Pseudomonas bacterial strain Pto DC3000 (Lee et al., Plant J, 54:452 (2008)) and rice DCW11 mediates mitochondrial signaling during pollen germination (Fujii et al., Plant Cell 2008). PP18 positively regulates drought and oxidative stress tolerance, but through an ABA-independent pathway in rice (You et al., Plant Physiol, 166:2100 (2014)).

Genes involved in the biosynthesis of secondary cell walls, including cellulose, hemicellulose and lignin are coordinately activated by transcription factors NACs, the top-level master switches, and MYBs, the second-level master switches (Nakano et al., Frontiers in plant science, 6:288 (2015); Zhong et al., Plant Cell Physiol, 56:195 (2015)). The secondary wall NAC domain proteins (SWNs) belong to a sub-group of the NAC family, and SWNs have been shown to regulate secondary wall biosynthesis in a few secondary wall-forming cell types in various plant species (Zhong et al., Plant Cell Physiol, 56:195 (2015)). In *Arabidopsis*, SWNs activate a battery of downstream transcription factors, and MYB46 and MYB83 are the two key transcription factors regulating secondary wall biosynthesis (Zhong et al., Plant Cell Physiol, 56:195 (2015)). In *Arabidopsis*, AC elements are present in promoters of almost all genes involved in lignin biosynthesis, and MYB46 and MYB83, bind to the AC elements and regulate the expression of most lignin biosynthesis genes during normal plant growth (Grima-Pettenati et al., Lignins: Biosynthesis, Biodegradation and Bioengineering, 61:173 (2012); Nakano et al., Frontiers in plant science, 6:288 (2015); Zhong et al., Plant Cell Physiol, 56:195 (2015)). The rice MYB46 and MTB83 homologs are not up-regulated by PP2CABA.

The structure of newly synthesized, stress-induced lignin has been found to be different from those of constitutively synthesized lignin (Cabane et al., Lignins: Biosynthesis, Biodegradation and Bioengineering, 61:219 (2012)), suggesting that lignin biosynthesis could be regulated by different signaling and metabolic pathways under normal and stressed conditions. In rice, SWN1 has been shown to be necessary for thickening of sclerenchyma cell walls, and loss-of-function of this gene leads to drooping leaf phenotype and reduced lignin and xylose contents (Yoshida et al., Frontiers in plant science, 4:383 (2013)). In this study, SWIN1 is highly activated by ABA and PP2CABA (FIG. 9A to FIG. 9B), suggesting that PP2CABA induces the expression of this particular NAC transcription factor for biosynthesis of lignin in response to osmotic stress.

Many NAC genes have also been shown to regulate biotic and abiotic stress tolerance in plants. Overexpression of three NACs, NAC5, NAC10 and NAC9/SNAC1, resulted in drought stress tolerance in transgenic rice, and enlarged root diameters in these plants are considered an important factor in reducing root metabolic costs, enhancing root water uptake and facilitating root downward penetration in dry soil (Jeong et al., Plant Physiol, 153:185, (2010); Jeong et al., Plant Biotechnol J 11:101 (2013); Redillas et al., Plant Biotechnol J, 10:792 (2012)). Neither the three NACs nor the NAC9/SNAC1-induced ABA-independent PP2C gene, PP18 (You et al., Plant Physiol, 166:2100 (2014)), was up-regulated by PP2CABA. However, ABA and overexpression of PP2CABA also enlarged the root diameter in rice (FIG. 5A-FIG. 5B), suggesting that root enlargement and drought stress tolerance are regulated by both ABA-dependent and ABA-independent pathways in rice.

Suberin and cuticle are the two major types of lipid polyesters found in plants. In *Arabidopsis*, mutants defective in the biosynthesis of suberin and cuticle results in enhanced seed coat permeability, decreased seed germination, and abnormal root growth under salt stress conditions (Beisson et al., Plant Cell, 19:351 (2007); Gou et al., P Natl Acad Sci USA, 106:18855 (2009)). In contrast, water use efficiency and drought tolerance are enhanced in a mutant with increased suberin accumulation (Franke et al., Frontiers in Plant Science, 3; 4 (2012)). Relatively less is known about the regulation of genes involved in suberin biosynthesis. In *Arabidopsis*, an abiotic stress-inducible MYB41 encoding an R2R3 MYB activates the expression of many genes involved in phenylpropanoid, suberin and cuticle biosynthesis, and enhance the accumulation of lignin, suberin and cuticle in mesophyll and epidermal cells in leaves (Kosma et al., Plant J, 80:216 (2014)). The MYB41 promoter is induced in endodermal and surrounding cortical cells in *Arabidopsis* roots by ABA and NaCl but inactive under unstressed growth conditions, indicating MYB41 may play a role in augmenting suberization under abiotic stress (Kosma et al., Plant J, 80:216 (2014)). However, the expression of the MYB41 homolog in rice is not activated by PP2CABA.

In transgenic *Arabidopsis*, overexpression of an ABA-inducible MYB96, which encodes an R2R3-type MYB transcription factor, reduces LR growth but promotes drought resistance, and the reduction in LR number is resulted from inhibition of LR emergence instead of LRP initiation (Seo et al., Plant Physiology, 151:275 (2009)). MYB96 transactivates and binds directly to promoters of several KCSs and other genes essential for biosynthesis of cuticular wax on leaf and stem surface and suberin in roots in *Arabidopsis* in response to ABA and drought stress (Seo et al., Plant Cell, 23:1138 (2011)). In this study, abundant extracellular lipids was deposited on the surface of roots overexpressing PP2CABA (FIG. 10B), and the expression of the rice MYB96 homolog was activated by ABA and PP2CABA (FIG. 9A to FIG. 9B). MYB96could be involved in the biosynthesis of suberin in response to abiotic stress in rice.

For application of PP2CABA to protect plants for survival throughout the drought stress period, an ABA- and abiotic stress-inducible promoter (Chen et al., Plant Biotechnol J, 13:105 (2015)) could be used to control the expression of PP2CABA. Alternatively, spray of plants with ABA or ABA analogs to transiently activate, or use of an inducible promoter to conditionally activate, the expression of PP2CABA may protect the primed crops from damages during drought stress conditions.

In summary, the studies described herein reveal an ABA signaling mechanism by which rice changes root architecture to adapt to water deficit stress.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of improving growth, stress tolerance and root architecture of a plant, comprising:
   (a) transforming plant cells with a DNA construct comprising an exogenous nucleic acid operably linked to a heterologous promoter, wherein the exogenous nucleic acid encodes short form type 2C protein phosphatase abscisic acid (PP2CABA) protein consisting of the amino acid sequence as set forth in SEQ ID NO: 4, to obtain transformed plant cells overexpressing said short form PP2CABA protein, and wherein said DNA construct and said exogenous nucleic acid do not encode long form PP2CABA protein having the amino acid sequence set forth in SEQ ID NO: 2;
   (b) growing said transformed plant cells obtained in step (a) to regenerate a plurality of transgenic plants overexpressing said short form PP2CABA protein; and
   (c) selecting a transgenic plant from said plurality of transgenic plants regenerated in step (b) that exhibits a lower lateral roots (LR) to primary roots (PR) ratio and a higher tolerance to abiotic osmotic or drought stress, as compared to (i) a control plant of the same species lacking said DNA construct and grown under identical growth conditions, and (ii) a transgenic plant overexpressing said long form PP2CABA protein and grown under identical growth conditions.

2. The method of claim 1, wherein the exogenous nucleic acid encoding short form PP2CABA protein comprises the nucleic acid sequence as set forth in SEQ ID NO: 3, which does not comprise the nucleic acid sequence as set forth in SEQ ID NO: 1.

3. The method of claim 1, wherein the heterologous promoter is selected from the group consisting of a constitutive promoter, a tissue-specific promoter, a developmental stage-specific promoter, and a promoter inducible by biotic or abiotic stress.

4. The method of claim 1, wherein the heterologous promoter is a constitutive promoter selected from the group consisting of a maize ubiquitin (Ubi) promoter, a rice actin (Act1) promoter, and a cauliflower mosaic virus 35S (CaMV35S) promoter.

5. The method of claim 1, wherein the heterologous promoter is a tissue-specific promoter selected from the group consisting of a rice glutelin (GluB) promoter, a rubisco small subunit (rbcS) promoter, and a maize zein gene promoter.

6. The method of claim 1, wherein the heterologous promoter is a developmental stage-specific promoter selected from the group consisting of a rice alpha-amylase (α-Amylase) promoter, and a rice glycine rich RNA binding protein (GRRP-A1) promoter.

7. The method of claim 1, wherein the heterologous promoter is a promoter inducible by biotic or abiotic stress, which is selected from the group consisting of an *Arabidopsis* rd29A promoter, an *Arabidopsis* corl SA promoter, an *Arabidopsis* kinl promoter, an *Arabidopsis* heat-shock factor (HSF) promoter, an *Arabidopsis* C-repeat-binding factor (CBF1) promoter, an *Arabidopsis* dehydration-responsive element binding protein (DREB1A) promoter, a rice HVA1 promoter, a rice HVA22 promoter, a rice PP2CABA promoter, an alcohol dehydrogenase (Adh) promoter, an ethanol-inducible promoter, an alpha-amylase promoter, and a synthetic ABRC321 promoter.

* * * * *